(12) United States Patent
Moskowitz

(10) Patent No.: US 11,521,240 B2
(45) Date of Patent: Dec. 6, 2022

(54) TRACKING A DIGITAL DIET FOR TARGETED ADVERTISEMENT DELIVERY

(71) Applicant: Aebeze labs, Palo Alto, CA (US)

(72) Inventor: Michael Phillips Moskowitz, Palo Alto, CA (US)

(73) Assignee: GetTogether, Inc., Berkeley, CA (US)

( * ) Notice: Subject to any disclaimer, the term of this patent is extended or adjusted under 35 U.S.C. 154(b) by 183 days.

(21) Appl. No.: 16/990,702

(22) Filed: Aug. 11, 2020

(65) Prior Publication Data

US 2020/0372544 A1 Nov. 26, 2020

Related U.S. Application Data

(63) Continuation-in-part of application No. 16/159,119, filed on Oct. 12, 2018, now Pat. No. 10,964,423, and a continuation-in-part of application No. 15/959,075, filed on Apr. 20, 2018, now Pat. No. 10,682,086, which is a continuation-in-part of application No. 15/702,555, filed on Sep. 12, 2017, now Pat. No. 10,261,991, said application No. 16/159,119 is a continuation-in-part of application No. 15/702,555, filed on Sep. 12, 2017, now Pat. No. 10,261,991.

(51) Int. Cl.
*G06Q 30/02* (2012.01)
*A61B 5/16* (2006.01)

(52) U.S. Cl.
CPC ..... *G06Q 30/0271* (2013.01); *G06Q 30/0245* (2013.01); *G06Q 30/0276* (2013.01); *G06Q 30/0277* (2013.01); *A61B 5/165* (2013.01)

(58) Field of Classification Search
CPC ........ G16H 20/70; G16H 40/67; G16H 50/20; G16H 50/30; G16H 10/60; G16H 80/00; G16H 50/00; G16H 50/70; G06F 40/30; G06F 40/284; G06F 40/211; G06F 40/216; G06F 40/35; G06F 40/56
See application file for complete search history.

(56) References Cited

U.S. PATENT DOCUMENTS

| | | | |
|---|---|---|---|
| 10,682,086 B2* | 6/2020 | Moskowitz | A61B 5/377 |
| 10,832,072 B1 | 11/2020 | Fraser | |
| 10,964,423 B2* | 3/2021 | Moskowitz | G16H 20/70 |
| 11,062,418 B2 | 7/2021 | Fraser | |
| 11,106,794 B2 | 8/2021 | Chow | |
| 11,157,700 B2* | 10/2021 | Moskowitz | G06F 40/30 |
| 2006/0064037 A1* | 3/2006 | Shalon | G16H 40/63 |
| | | | 128/903 |

(Continued)

FOREIGN PATENT DOCUMENTS

EP 3096506 11/2016

*Primary Examiner* — Vijay B Chawan
(74) *Attorney, Agent, or Firm* — Patent Ventures, LLC

(57) ABSTRACT

The present invention comprises of receiving a text input comprising message content from an electronic computing device associated with a user; parsing the message content comprised in the text input for emotionally-charged language; assigning a sentiment value, based on the emotionally-charged language, from a dynamic sentiment value spectrum to the text input; and, based on the sentiment value, imposing a sentiment vector, corresponding to the assigned sentiment value, to the text input, the imposed sentiment vector rendering a sensory effect on the message content designed to convey a corresponding sentiment.

35 Claims, 30 Drawing Sheets

(56) References Cited

U.S. PATENT DOCUMENTS

| | | | | |
|---|---|---|---|---|
| 2011/0004483 A1* | 1/2011 | Ting | ............ | G06F 16/951 |
| | | | | 707/E17.108 |
| 2011/0125063 A1* | 5/2011 | Shalon | ............ | A61B 5/0006 |
| | | | | 600/590 |
| 2017/0319123 A1* | 11/2017 | Voss | ............ | A61B 5/6803 |
| 2020/0053030 A1* | 2/2020 | Moskowitz | ......... | G06F 16/9535 |
| 2020/0348807 A1 | 5/2020 | Garcia et al. | | |
| 2020/0265941 A1* | 8/2020 | Moskowitz | ............ | G16H 40/63 |
| 2021/0125703 A1* | 4/2021 | Moskowitz | ............ | G16H 50/20 |

* cited by examiner

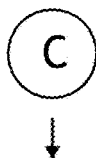

| | |
|---|---|
| based on the sentiment value, imposing a sentiment vector, corresponding to the assigned sentiment value, to the text input, the imposed sentiment vector rendering a sensory effect on the message content designed to convey a corresponding sentiment | S140 |
| the sensory effect rendered by the sentiment vector includes one of color change of a component of the message content, change in text font of a component of the message content, audio effect, haptic effect, and graphical addition to the message content | S141 |
| the sentiment vector imposed to the text input is a voice accompaniment | S142 |

FIG. 8D

CONTENT TYPE

☒ Video
☐ Music
☐ Film clip
☐ GIF
☐ Photo
☐ PDF
☐ Screen shot
☐ Social media post
☐ Text message template
☐ AR asset
☐ VR asset

TREATMENT TYPE

☐ Amaze
☐ Happy
☐ Hopeful
☐ Sad
☐ Lonely
☐ Tired
☐ Energy / Energize
☒ Focus
☐ Calm
☐ Connection
☐ Confidence
☐ Anti-Anxiety / Stress-Control
☐ Story / Entertainment
☐ Experimental Medicine

FIG. 19

Users can tap to see drug information, benefits, and citations.

SEROTONIN

Content should: Regulate mood and provide stability for happiness to flourish

Benefits: Mood stability | Sleep | Appetite | Sexual Performance

How to activate:

- Exercise
- Humor/laughter
- Motivation (curiosity, learning, memory)
- Gratitude
- Delayed reward

QUICK REFERENCE

Animals: oxytocin
Art: dopamine
Audio stimulation: dopamine
Calming: GABA
Connection: oxytocin
Curiosity: Cocktail of dopamine + serotonin
Cuteness: oxytocin
Empathy: oxytocin
Exercise: endorphins + dopamine + serotonin
Focus: acetylcholine + dopamine
Food: Viewing: GABA | Consuming: *depends on food*
Games: acetylcholine
Gratitude: Cocktail of dopamine + serotonin
Helping others: oxytocin
Humor: Cocktail of dopamine + serotonin + endorphins

Laughter: Cocktail of dopamine + serotonin + endorphins
Learning: acetylcholine + dopamine + serotonin
Love: oxytocin
Meditation: GABA
Memory: acetylcholine + serotonin
Music: dopamine
Nostalgia: experimental medicine
Physical movement: endorphins + dopamine + serotonin
Self-talk/affirmations: dopamine
Self-disclosure: dopamine
Sleep: Cocktail of GABA + dopamine + serotonin + acetylcholine
Social touch: oxytocin + endorphins
Questions: dopamine
Visual stimulation: dopamine

FIG. 23

TRACKING A DIGITAL DIET FOR TARGETED ADVERTISEMENT DELIVERY

TECHNICAL FIELD

This invention relates generally to the field of electronic communications and the transmittance of such communications. More specifically, the invention discloses a new and useful method for self-rating and autonomously rating a therapeutic value to digital content. Further, tracking a digital diet of a user based on consumption of the labeled content for targeted delivery of an advertisement.

BACKGROUND

In the past few decades, the availability and use of electronic computing devices, such as desktop computers, laptop computers, handheld computer systems, tablet computer systems, and cellular phones have grown tremendously, which provide users with a variety of new and interactive applications, business utilities, communication abilities, and entertainment possibilities.

One such communication ability is electronic messaging, such as text-based, user-to-user messages. Electronic messaging has grown to include a number of different forms, including, but not limited to, short message service (SMS), multimedia messaging service (MMS), electronic mail (e-mail), social media posts and direct messages, and enterprise software messages. Electronic messaging has proliferated to such a degree that it has become the primary mode of communication for many people.

While electronic messaging can be a particularly efficient mode of communication for a variety of reasons—instant delivery, limitless distance connectivity, recorded history of the communication—electronic messaging does not benefit from the advantages of in-person communication and telecommunication. For example, when communicating via telecommunication, a person can adjust, alter, or augment the content of their message to an intended recipient through tone, volume, intonation, and cadence. When communicating in-person, or face-to-face, a person can further enhance or enrich their spoken words with eye contact and shift of focus, facial expressions, hand gestures, body language, and the like. In electronic messaging, users lack these critically important signals, clues, and cues, making it difficult for people to convey the subtler aspects of communication and deeper intent. As a result, issues of meaning, substance, and sentiment are often lost or confused in electronic messages, which can, and very often does, result in harmful or damaging misunderstandings. Miscommunications can be particularly damaging in interpersonal and business relationships.

Another unintended effect of our overreliance on electronic communication is the impairment of emotional and mental health. In a recent article published in the American Journal of Psychiatry, Dr. Jerald Block wrote "technology addiction is now so common that it merits inclusion in the Diagnostic and Statistical Manual of Mental Disorders, the profession's primary resource to categorize and diagnose mental illnesses." He went on to further state that the disorder leads to anger and depression when the tech isn't available, as well as lying, social isolation and fatigue. Our devices and experiences from said devices (receiving likes, comments and shares on social media) are in essence a drug dealer and drugs, respectively: Having the capability of doling out the same kind of dopamine hit as a tiny bump of cocaine. In effect, creating the typical addiction/dependency vicious cycle and all of the attendant consequences.

According to psychotherapist, Nancy Colier, author of "The Power of Life", "We are spending far too much of our time doing things that don't really matter to us . . . [and become] disconnected from what really matters, from what makes us feel nourished and grounded as human beings." Based on her findings, the average person checks their smartphones 150 times per day, or every six minutes. Furthermore, the average young adult sends on average 110 texts per day and 46% of respondents checked that their devices are something that they couldn't live without.

With this kind of digital ubiquity, it is becoming readily apparent that any solution to the problem involving curtailing or augmenting user behavior is not a realistic approach. Current approaches espoused by experts involve any one of, or combination of, the following: Downloading an app (Moment, Alter, etc.) that locks or limits phone usage upon reaching a pre-specified limit; disabling notifications from your phone settings; keeping the blue-hued light of your smartphone away from your place of rest; and even buying and carrying around a dummy phone.

There is a void for a solution that takes into account ubiquitous usage and provides delivery of pro-mental and emotional health content—personalized to the user, much like the way therapeutics have become narrowly tailored—to counter all of the digital-mediated ill effects plaguing our society. These effects will only logarithmically grow as we transition into the IoT era—where we will be exposed to thousands of internet-enabled objects (each capable of delivering contextualized analytics and provisioning) as part of our day-to-day living.

What's more, there is a void for a solution that allows for a self-generated or system-generated rating for therapeutic value of digital content. In other words, currently, there is no technological solution for a standardized rating of digital content based on its psycho-emotional effects on the targeted user or a general user. Furthermore, there is currently no solution with downstream provisioning of digital/interactive content based on the rated content. Furthermore, there lacks a means for tracking a user's consumption of labeled digital content (indicator of intended psycho-emotional effect) for a more targeted and personalized advertisement delivery/experience.

SUMMARY

Disclosed is a method and system for imposing a dynamic sentiment vector to an electronic message. In one embodiment of the invention, the method comprises: receiving a text input comprising message content from an electronic computing device associated with a user; parsing the message content comprised in the text input for emotionally-charged language; assigning a sentiment value, based on the emotionally-charged language, from a dynamic sentiment value spectrum to the text input; and, based on the sentiment value, imposing a sentiment vector, corresponding to the assigned sentiment value, to the text input, the imposed sentiment vector rendering a sensory effect on the message content designed to convey a corresponding sentiment.

In another embodiment of the invention, the method comprises: receiving a text input comprising message content from an electronic computing device associated with a user; converting the message content comprised in the text input received from the electronic computing device into converted text in a standardized lexicon; parsing the converted text for emotionally-charged language; generating a sentiment value for the text input from a dynamic sentiment value spectrum by referencing the emotionally-charged language with a dynamic library of emotionally-charged language; and, based on the sentiment value, imposing a sentiment vector to the text input, the imposed sentiment vector rendering a sensory effect on the message content designed to convey a corresponding sentiment.

For example, in one application of the invention, a user can write and submit a text message on the user's cellular phone for delivery to the user's best friend. After receiving the text message, the invention can analyze the message content of the text message and determine, based on the verbiage, syntax, and punctuation within the message content, that the user is attempting to convey excitement through the text message. The invention can then apply a visual filter of red exclamation points or other illustrative, performative, or kinetic attributes to the text message, indicating the excitement of the user, before the text message is delivered to the user's best friend.

In another example of one application of the invention, a user can write and submit a direct message through a social media application (e.g., Instagram, Facebook, SnapChat) on the user's mobile phone for delivery to a second user. After receiving the direct message, the invention can use a camera built into the user's mobile phone to capture an image of the user's face and analyze aspects of the user's face (e.g., curvature of the lips, motion of the eyes, etc.) to determine the user's mood or expression. Based on the user's mood or expression, the invention can then apply a vibration pattern to the direct message before the direct message is delivered to the second user.

In another object of the invention, sentiment and cues of the users emotional or mental state is not gleamed by referencing a parsed user input against a dynamic library of emotionally-charged language to generate a sentiment value and vector for overlaying the said input. Rather, the emotional and mental state (EMS) of the user is chosen by the user or determined by the system based on user engagement with the interface or content. Once the EMS of the user is defined, carefully curated and efficacious content is delivered to the user to combat the defined EMS.

In one aspect, a method is provided for delivering a digital therapeutic, specific to a user-chosen emotional or mental state (EMS), the method comprising the steps of: recognizing at least one EMS selected by the user from a plurality of EMS, the selected EMS indicating at least one of a feeling, sensation, type of discomfort, mood, mental state, emotional condition, or physical status of the user. Once the EMS is defined, the method then calls for pushing a primary-level message personalized to the user based on at least one stored message coupled to the selected EMS. Finally, pushing at least a secondary-level message personalized to the user based on a threshold-grade match of the user response to the pushed primary-level message with at least one stored response coupled to a stored primary-level message, whereby the user and stored response is a measure of at least one of a reaction, compliance, engagement, or interactivity with the pushed and, or stored primary-level message. The primary and secondary-level messages may contain at least one of a text, image, sound, video, art asset, suggested action or recommended behavior. The efficaciousness or therapeutic value of the primary or secondary messages are validated by at least one—and typically two—independent sources of clinical research or peer-reviewed science, as verified by a credentialed EMS expert.

In another aspect, once the EMS is defined, the method may call for pushing at least a single-level message. The at least single message may contain at least one of a text, image, sound, video, art asset, suggested action or recommended behavior. Again, the efficaciousness or therapeutic value of the primary or secondary messages are validated by at least one—and typically two—independent sources of clinical research or peer-reviewed science, as verified by a credentialed EMS expert.

In yet another aspect, a system is described and claimed for delivering the digital content of validated therapeutic efficacy. The system may comprise an EMS store; at least a primary message prescriber; a processor coupled to a memory element with instructions, the processor when executing said memory-stored instructions, configure the system to cause: at least one EMS from a plurality of EMS in the EMS store to be selected by the user, said selected EMS indicating at least one of a feeling, sensation, type of discomfort, mood, mental state, emotional condition, or physical status of the user; and the at least primary message prescriber pushing a primary-level message personalized to the user based on at least one stored message coupled to the selected EMS.

In yet other aspects, at least a secondary message prescriber is included, wherein the at least secondary message prescriber pushes at least a secondary-level message personalized to the user based on a threshold-grade match of the user response to the pushed primary-level message with at least one stored response coupled to a stored primary-level message, whereby the user and stored response is a measure of at least one of a reaction, compliance, engagement, or interactivity with the pushed and, or stored primary-level message.

In both aspects (primary or at least secondary message prescribers), the messages or content may contain at least one of a text, image, sound, video, art asset, suggested action or recommended behavior. Much like in the method aspects, the therapeutic value of the messages or content are validated by at least one—and typically two—independent sources of clinical research or peer reviewed published science and selected by a credentialed EMS expert.

Whether the sentiment or cues are generated by the system or defined by the user, content is being overlaid or delivered to enhance intonation, heighten digital communication, obviate ambiguity, boost mood, support self-esteem, inspire wellness, and aid in the longitudinal and non-interventional care for people in distress or need—leveraging a familiar and known modality (digital devices). According to the claimed invention, a whole ecosystem of receiving and delivering modalities are provided for a host of digital therapeutics. The digital therapeutic offerings—with the aid of Artificial Intelligence (AI), machine learning, and, or predictive EMS assessment tools—may deliver increasingly personalized solutions uniquely tailored to aid each subscriber. Such non-interventional, anonymous, and device-centric solutions are far more appropriate to combat the rising ill-effects of device dependency—rather than pharmaceutical dosing, in-patient treatment, and altering device behavior.

In another aspect of the invention, the user or system may generate a rating for a therapeutic value of digital content. The claimed invention claims and discloses a technological solution for a standardized rating of digital content based on its psycho-emotional effects on the targeted user or a general user. The user may then engage with the content accordingly. Forms of engagement may be suggested, prompted, or pushed based on the uploaded and rated content. It is one object to enable a system and method for labeling a therapeutic value to digital content, said method comprising the steps of uploading a digital content by a user; selecting at least one condition from a plurality of conditions that the uploaded digital content is intended to cure, said selected condition indicating at least one of a feeling, sensation, mood, mental state, physical state, emotional condition, physical status; and overlaying a therapeutic label to the digital content corresponding to the selected condition.

It is another object to disclose and claim a method and system, wherein said system comprises of a condition selector, a therapeutic labeler, a non-transitory storage element coupled to the processor wherein the encoded instructions when implemented by the processor, configure the digital therapeutic value pipeline to: upload a digital content by a user; select at least one condition from a plurality of conditions that the uploaded digital content is intended to cure by the condition selector, said selected condition indicating at least one of a feeling, sensation, mood, mental state, physical state, emotional condition, physical status; and overlay a therapeutic label to the digital content corresponding to the selected condition by the therapeutic labeler.

In another aspect of the invention, the digital content, labeled in terms of its determined intended psycho-emotional effect on the user, is further tracked by a Digital Nutrition (DN) tracker to assess a DN diet score for the user. The score may be an at-the-moment score or more longitudinal, reflecting the users media consumption habits for a more targeted delivery of an advertisement.

BRIEF DESCRIPTION OF DRAWINGS

FIGS. 8A, 8B, 8C, and 8D is a graphical representation of one embodiment of the electronic messaging system. are flow diagrams of one embodiment of the electronic messaging system.

FIG. 19 illustrates a representative screen shot of an initiating sequence of the therapeutic labeler system in accordance with an aspect of the invention.

FIG. 23 illustrates a quick reference guide of therapeutic labeler in accordance with an aspect of the invention.

DETAILED DESCRIPTION OF DRAWINGS

Numerous embodiments of the invention will now be described in detail with reference to the accompanying figures. The following description of the embodiments of the invention is not intended to limit the invention to these embodiments but rather to enable a person skilled in the art to make and use this invention. Variations, configurations, implementations, and applications described herein are optional and not exclusive to the variations, configurations, implementations, and applications they describe. The invention described herein can include any and all permutations of these variations, configurations, implementations, and applications.

In the following description, numerous specific details are set forth in order to provide a thorough understanding of the invention. It will be apparent, however, to one skilled in the art that the invention can be practiced without these specific details.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but no other embodiments.

Figure 1:
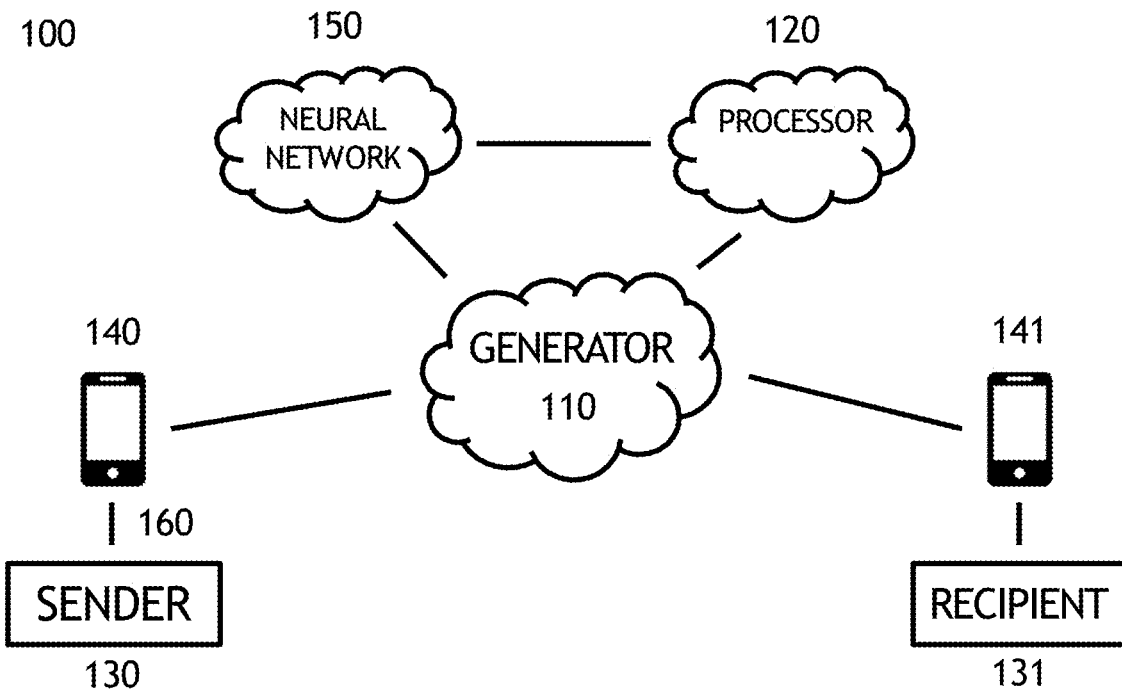
FIG. 1 is a graphical representation of one embodiment of the electronic messaging system.

FIG. 1 depicts a schematic of a system 100 for imposing a dynamic sentiment vector to an electronic message. In one embodiment, a system 100 can include: a sentiment vector generator 110, a processor 120, and an electronic computing device 140 associated with a particular user 130. The sentiment vector generator 110, the processor 120, and the electronic computing device 140 are communicatively coupled via a communication network. The network may be any class of wired or wireless network including any software, hardware, or computer applications that can provide a medium to exchange signals or data. The network may be a local, regional, or global communication network.

The electronic computing device 140 may be any electronic device capable of sending, receiving, and processing information. Examples of the computing device include, but are not limited to, a smartphone, a mobile device/phone, a Personal Digital Assistant (PDA), a computer, a workstation, a notebook, a mainframe computer, a laptop, a tablet, a smart watch, an internet appliance and any equivalent device capable of processing, sending and receiving data. The electronic computing device 140 can include any number of sensors or components configured to intake or gather data from a user of the electronic computing device 140 including, but not limited to, a camera, a heart rate monitor, a temperature sensor, an accelerometer, a microphone, and a gyroscope. The electronic computing device 140 can also include an input device (e.g., a touchscreen or a keyboard) through which a user may input text and commands.

As further described below, the sentiment vector generator 110 is configured to receive an electronic message 160 (e.g., a text input) from the particular user 130 associated with the electronic computing device 140 and run a program 116 executed by the processor 120 to analyze contents of the electronic message, determine a tone or a sentiment that the particular user 130 is expressing through the electronic message 160, and apply a sentiment vector to the electronic message 160, the sentiment vector designed to convey the tone or sentiment determined by the sentiment vector generator 110. The electronic message 160 can be in the form of a SMS message, a text message, an e-mail, a social media post, an enterprise-level workflow automation tool message, or any other form of electronic, text-based communication. The electronic message 160 may also be a transcription of a voice message generated by the particular user 130. For example, in one embodiment, from a messaging application installed on the electronic computing device 140, the user 130 may select to input a voice (i.e., audio) message through a microphone coupled to the electronic computing device 140 or initiate a voice message through a lift-to-talk feature (e.g., the user lifts a mobile phone to the user's ear and the messaging application automatically begins recording a voice message). In this example, the system 100 can generate a transcription of the voice message or receive a transcription of the voice message from the messaging application. After receiving or generating the transcription (i.e., an electronic message), the sentiment vector generator 110 can then analyze the message content within the electronic message, determine the mood or sentiment of the message content, and apply a corresponding sentiment vector to the electronic message, as further described below.

In one embodiment, the system 100 may receive an electronic message 160 in the form of an electroencephalograph (EEG) output. For example, in this embodiment, a user can generate a message using an electronic device communicatively coupled to the user and capable of performing an electroencephalograph to measure and record the electrochemical activity in the user's brain. In this example, the system 100 can transcribe the EEG output into an electronic message 160 or receive a transcription of the EEG output from the electronic device communicatively coupled to the user. After receiving or generating the electronic message 160 from the EEG, the sentiment vector generator 110 can then analyze the message content within the electronic message 160, determine the mood or sentiment of the message content, and apply a corresponding sentiment vector to the electronic message. In one example of this embodiment, a user is connected to an augmented reality (AR) or virtual reality (VR) headset capable of performing an EEG or an equivalent brain mapping technique. The user can generate a message simply by thinking of what the user is feeling or would like to say. The headset can monitor and record these thoughts and feelings using the EEG and transcribe the thoughts and feelings into an electronic message or send the EEG output signals directly to the system 100. The system 100 can then analyze the message content included within the electronic message 160, determine the mood or sentiment of the message content, and apply a corresponding sentiment vector to the electronic message 160, creating a vectorized message. The system 100 can then send the vectorized message to the user's intended recipient (e.g., a recipient that the user thought of).

In one embodiment, the particular user 130 may submit an electronic message 160 through a mobile application (e.g., a native or destination app, or a mobile web application) installed on the particular user's mobile phone or accessed through a web browser installed on the user's phone. In one example of this embodiment, the user accesses the mobile application, submits the electronic message 160 in the form of a text input. The sentiment vector generator 110 can then analyze the message content included within the electronic message 160, determine the mood or sentiment of the message content, and apply a corresponding sentiment vector to the electronic message 160, creating a vectorized message. In this example, the user can then send the vectorized message to the user's intended recipient(s) 131 (e.g., by copying and pasting the vectorized message into a separate messaging application or selecting to export the vectorized message to a separate application, as further described below). In one variation of this embodiment, the user may send the vectorized message to the intended recipient 131 directly through the mobile application. In one embodiment, the user may submit an electronic message 160, or a component of an electronic message (e.g., a single word or phrase within the message content of an electronic message) using a touch input gesture. In one example of this embodiment, the user may submit the electronic message 160 through an electronic computing device by swiping a finger on a touch screen coupled to the electronic computing device 140 in a U-shaped gesture on the electronic message.

In another embodiment, the user may input an electronic message 160 into an entry field of a third-party application such as an email client (e.g., Gmail, Yahoo Mail) or a social media application (e.g., Facebook, Twitter, Instagram). For example, the user may input a message into the body of an email, or into a status update on Facebook. In this embodiment, the system 100 can detect the input of the electronic message 160 into the third-party application and upload the electronic message 160 to the sentiment vector generator 110. The sentiment vector generator 110 can then analyze the message content contained within the electronic message 160, determine the mood or sentiment of the message content, and apply a corresponding sentiment vector to the electronic message 160, creating a vectorized message. The sentiment vector 110 can then replace the electronic message 160 within the third-party application with the vectorized message. Alternatively, the user may select to replace the electronic message 160 with the vectorized message (e.g., by copying and pasting the vectorized message into the entry field).

Figure 2:
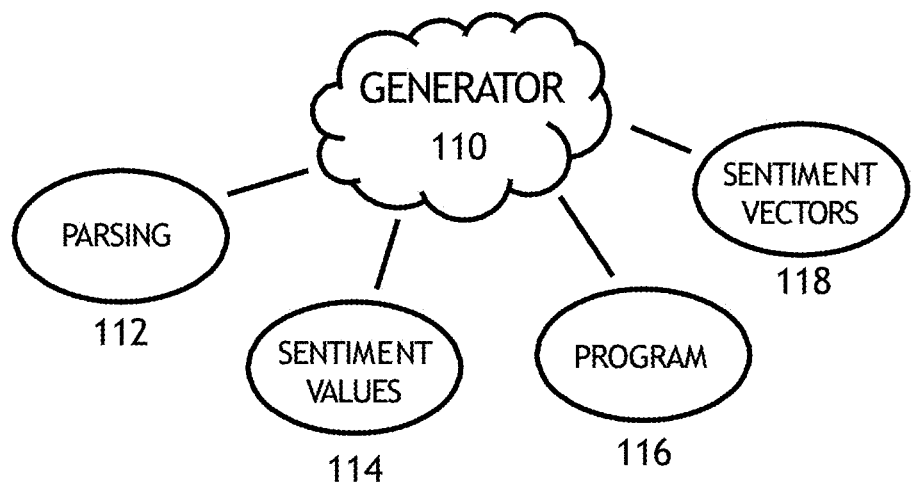
FIG. 2 is a graphical representation of one embodiment of the electronic messaging system.

FIG. 2 depicts a [schematic] of the sentiment vector generator 110. In one embodiment, the sentiment vector generator 110 includes a parsing module 112, a dynamic sentiment value spectrum 114, a program 116, and a library of sentiment vectors. In this embodiment, after receiving an electronic message 160, the sentiment vector generator 110 can activate the program 116 executed by a processor 120 to analyze message content contained within the electronic message 160 using the parsing module 112, the sentiment value spectrum 114, and the library of sentiment vectors, which are discussed in further detail below. Part or all of the sentiment vector generator 110 may be housed within the electronic computing device 140. Likewise, part of all of the sentiment vector generator 110 may be housed within a cloud computing network.

Figure 3A:
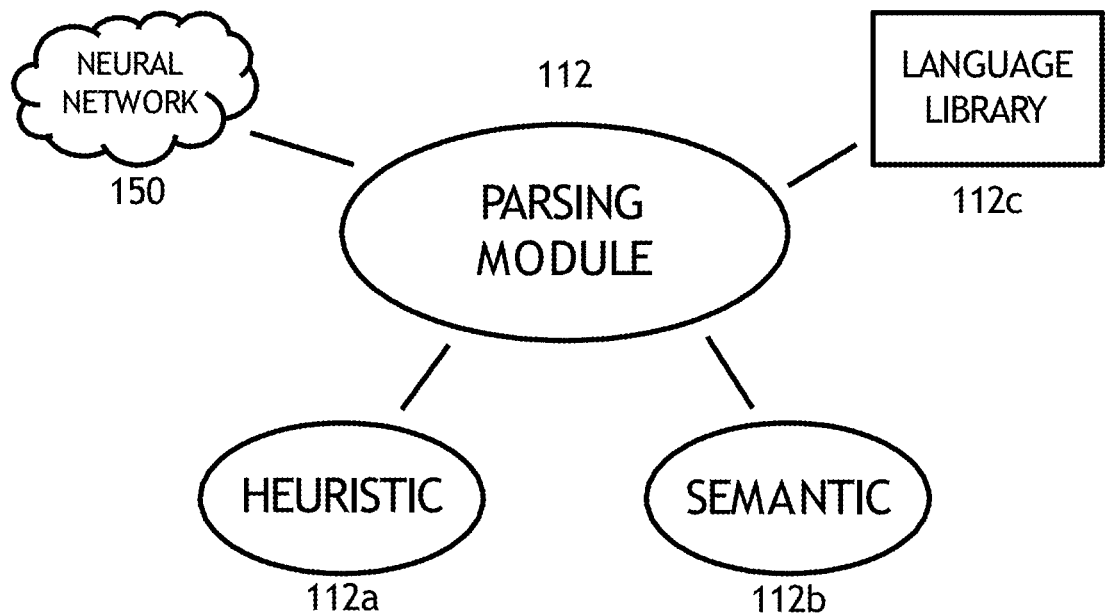
FIGS. 3A and 3B are graphical representations of one embodiment of the electronic messaging system.
Figure 3B:
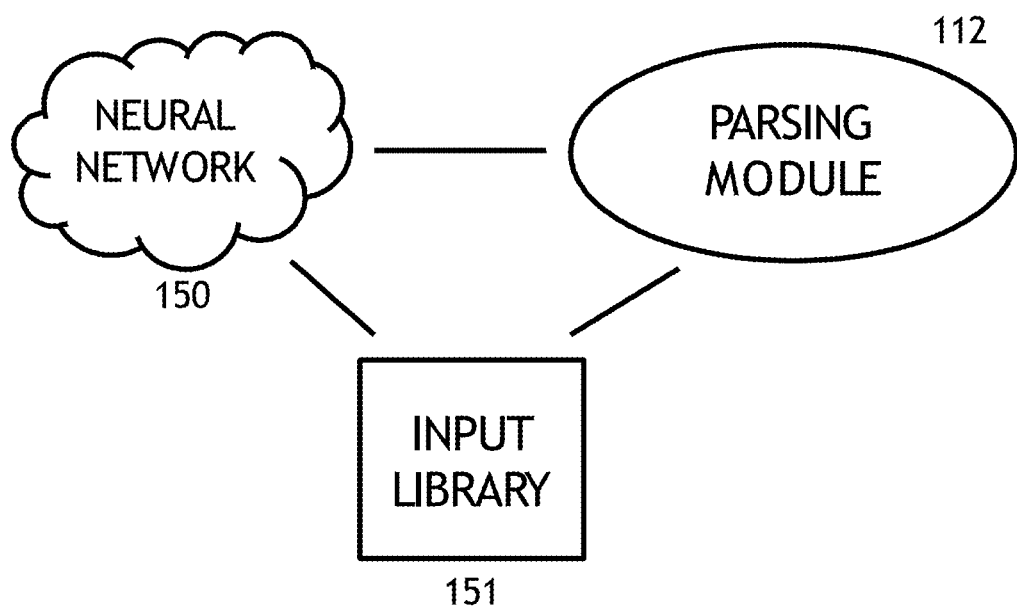

FIG. 3 depicts a schematic of the parsing module 112. The parsing module 112 is configured to parse message content contained within an electronic message 160 received by the sentiment vector generator 110 for emotionally-charged language and determine a sentiment value for the electronic message 160 from the dynamic sentiment value spectrum 114. In one embodiment, the parsing module 112 can include one or both of a heuristic layer 112a and a semantic layer 112b. The heuristic layer 112a is configured to recognize, within the message content contained within the electronic message 160, shorthand script, symbols, and emotional icons (emoticons). For example, the message "r u okay?:(" contains the shorthand character "r" to represent the word "are," the shorthand character "u" to represent the word "you," and the emoticon ":(," representing an unhappy face, each of which the heuristic layer 112a is configured to recognize. The heuristic layer 112a can be further configured to translate recognized shorthand script, symbols, and emoticons into a standardized lexicon. For example, referring back to the previous example, the heuristic layer can translate "u" into "you," "r" into "are," and ":(" into "[sad]." The heuristic layer 112a can thus translate the entire message from "r u okay?:(" to "are you okay? [sad]" in order to compare the sentiments expressed within different messages in a more objective manner and determine the nature of the emotionally-charged language contained within the message of content of the electronic message 160.

The semantic layer 112b is configured to recognize, within the message content contained within the electronic message 160, natural language syntax. For example, in the message "is it ok if we text on WhatsApp?" the construction of the phrases "is it ok" and "WhatsApp?" reflect natural language syntax that can express particular sentiments. "is it ok[?]" can express tentativeness in addition to the objective question that the phrase asks. For reference, inverting and contracting the first two words to create the phrase "it's okay[?]" results in a phrase that can express more confidence. Likewise, the space inserted between "WhatsApp" and "?" can have the effect of "softening" the question mark in comparison to "WhatsApp?" The semantic layer 112b is configured to recognize the use of natural language syntax such as "is it ok" and "WhatsApp?" and can be further configured to translate the recognized natural language syntax into a standardized lexicon. The standardized lexicon can be a standard set of words and terms (e.g., an Oxford dictionary) that the parsing module 112 is able to parse for emotionally-charged language. In one embodiment, the standardized lexicon is a standard set of words and terms with predefined attributes. For example, again referring to the previous example, the semantic layer 112b can translate the entire message from "is it ok if we text on WhatsApp?" to "can[soft] we text on WhatsApp?[soft]" in order to compare the sentiments expressed within different messages in a more objective manner and determine the nature of the emotionally-charged language contained within the message of content of the electronic message 160.

In one embodiment, the parsing module 112 can include a library of emotionally-charged language 112c. In this embodiment, after parsing the message content contained within the electronic message 160, the parsing module 112 can cross-reference the words and terms contained with the message content to the library of emotionally-charged language 112c. The words and terms contained within the library of emotionally-charged language 112c may be tagged with attributes according to the sentiments they most commonly express. For example, the library of emotionally-charged language 112c may include the terms "disastrous," "splendid," "terrible," and "awesome." Within the library of emotionally-charged language 112c, "disastrous" may be tagged with the attribute [bad] or [negative]; "splendid" may be tagged with the attribute [good] or [positive]. In one embodiment, the terms contained within the library of emotionally-charged language 112c may additionally or alternatively be tagged with a numeric value. For example, "disastrous" may be tagged with the attributes [negative; 7], and "terrible" may be tagged with the attributes [negative; 5], indicating that while "disastrous" and "terrible" may express similar "negative" sentiments, "disastrous" is more negative than "terrible." In one embodiment, the parsing module 112 (or, alternatively, any component of the system 100) can dynamically add or remove words or terms to and from the library of emotionally-charged language 112c. The parsing module 112 may use any technique to tag or evaluate the sentiments of emotionally-charged language.

In one embodiment, the library of emotionally-charged language 112c is specific to the particular user 130. In this embodiment, each particular user 130 of the system 100 access a unique library of emotionally-charged language 112c associated only with that particular user. In one variation of this embodiment, the particular user 130 may manually add or remove words and terms to and from the library of emotionally-charged language 112c. In one embodiment of the system 100, the system 100 can be accessed by multiple users. In one variation of this embodiment, the library of emotionally-charged language 112c employed by the parsing module 112 is the same for each user.

In one embodiment of the system 100, the parsing module additionally includes a neural network 150 and a library of inputs 151. In this embodiment, after parsing the message content of an electronic message 160 received by the sentiment vector generator 11, the parsing module 112 can store the electronic message 160 in the library of inputs 151, along with the emotionally-charged language found within the message content and any accompanying attributes, creating a database of messages and their accompanying emotionally-charged language. In this embodiment, the neural network 150 can employ machine learning techniques to analyze this database for patterns and trends in order to dynamically improve the performance of the sentiment vector generator 110. For example, the neural network 150 may determine through the application of an algorithm that the particular user 130 uses the term "disastrous" ten times more often than the particular user 130 uses the term "terrible." Thus, even though "disastrous" may be a more negative term than "terrible" for the average user or person, the neural network can determine that, for the particular user 130, "disastrous" generally carries less emotional weight than "terrible." In this example, the neural network 150 can then update the parsing module 112 and the library of emotionally-charged language accordingly. For example, in the example in which the terms "disastrous" and "terrible" begin as tagged within the library of emotionally-charged language 112c as [negative; 7] and [negative; 5], respectively, the neural network 150 can update the attributes to read [negative; 5] and [negative 7], respectively. In one embodiment, the parsing module 112 can store electronic messages into the library of inputs 151 along with their standardized lexicon conversions.

FIG. 4 depicts graphical representations of the parsing of electronic messages by the parsing module 112. FIG. 4A depicts the parsing of three separate electronic messages 160, "it definitely has given me more time and flexibility and channels creativity differently" 160a, "is it ok if we text on WhatsApp?" 160b, and "Oh u live in Williamsburg" 160c for emotionally-charged language by the parsing module 112. In, this example, in the message content of 160a, the parsing module 112 determines three emotionally-charged words and terms: "definitely has," "and," and "differently;" in the message content of 160b: "ok," "we," and "WhatsApp?" and in the message content of 160c: "u" and "Williamsburg." In one embodiment, as discussed above, after parsing the message content, the parsing module 112 can determine attributes for the emotionally-charged language found in the message content, as depicted by S123 in FIG. 4B. In the example depicted in FIG. 4B, the parsing module 112 tags "definitely has" with [positive, active], "and" with [neutral], and "differently" with [negative]. In one embodiment, as discussed above, the parsing module 112 includes a semantic layer 112b configured to recognize, within the message content contained within the electronic message 160, natural language syntax, as depicted by S122 in FIG. 4B. In the example depicted in FIG. 4B, the semantic layer 112b recognizes the space between "WhatsApp" and "?" in "is it ok if we text on WhatsApp?" as an instance of natural language syntax. In one embodiment, as discussed above, the parsing module 112 includes a heuristic layer 112a configured to recognize, within the message content contained within the electronic message 160, shorthand script, symbols, and emoticons, as depicted by S124 in FIG. 4B. In the example depicted in FIG. 4B, the heuristic layer 112a recognizes "u" as a shorthand term for "you."

Figure 4A:
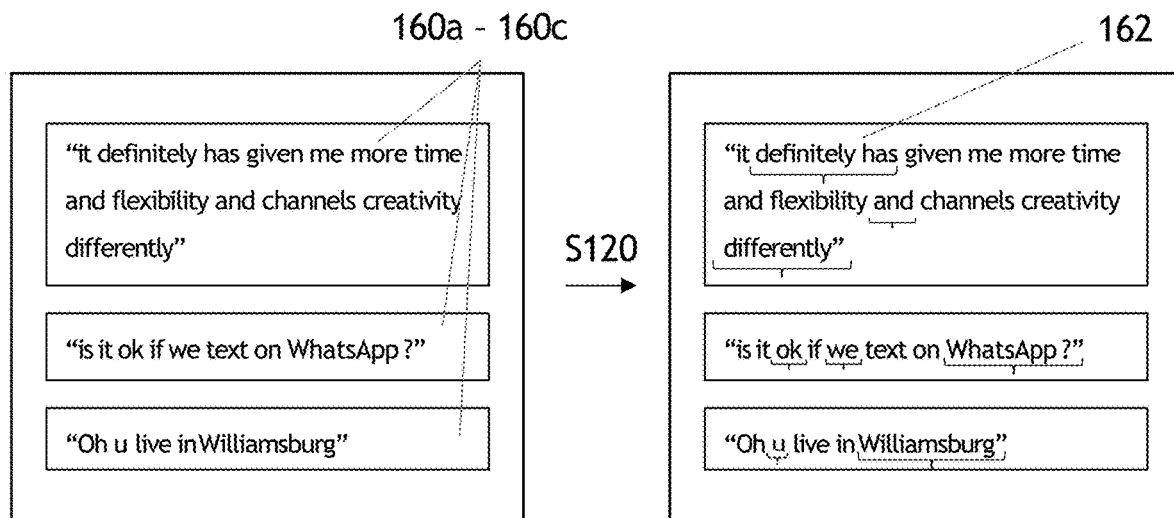
FIGS. 4A, 4B, 4C and 4D are graphical representations of one embodiment of the electronic messaging system.
Figure 4B:
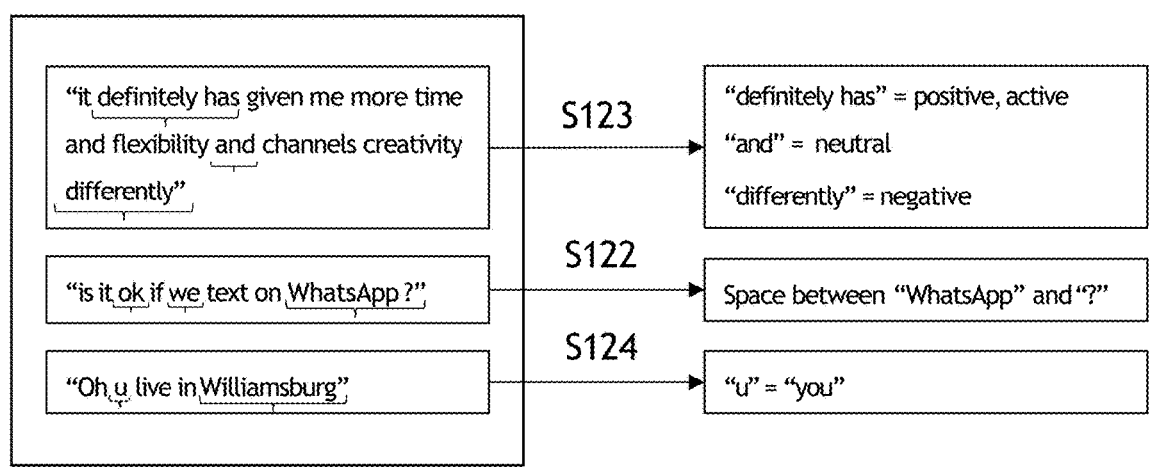
Figure 4C:
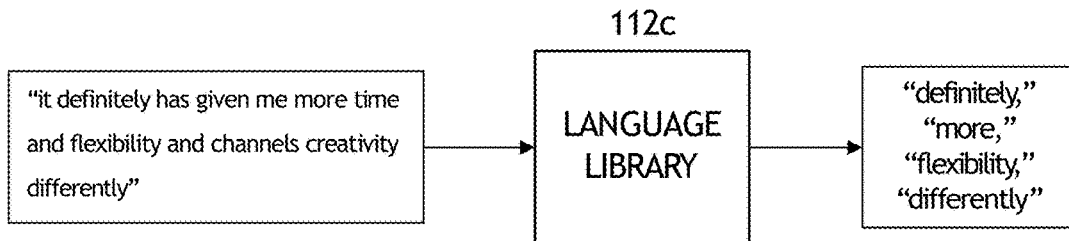
Figure 4D:
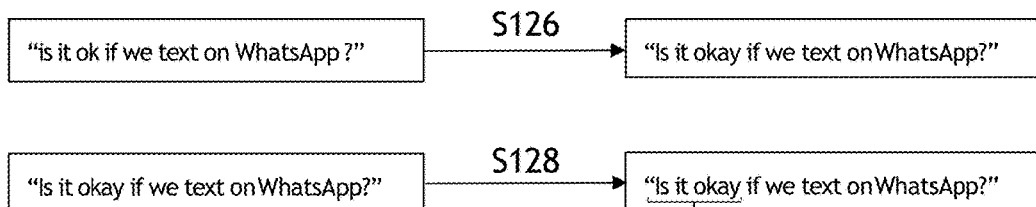

In one embodiment, as discussed above, after parsing the message content contained within the electronic message 160, the parsing module 112 can cross-reference the words and terms contained with the message content to a library of emotionally-charged language 112c, as depicted in FIG. 4C. In the example depicted in FIG. 4C, the parsing module 112 cross-references electronic message 160a with the library of emotionally-charged language 112c and determines that "differently," "more," "flexibility," and "differently" are emotionally-charged words or terms. In one embodiment, as discussed above, before parsing the message content of an electronic message 160, the parsing module 112 can convert the message content into a standardized lexicon, as depicted in FIG. 4D. In the example depicted in FIG. 4D, the parsing module 112 converts "is it ok if we text on WhatsApp?" into the converted text, "is it okay if we text on WhatsApp?" in step S126 before parsing the converted text for emotionally-charged language in step S128.

Figure 5A:
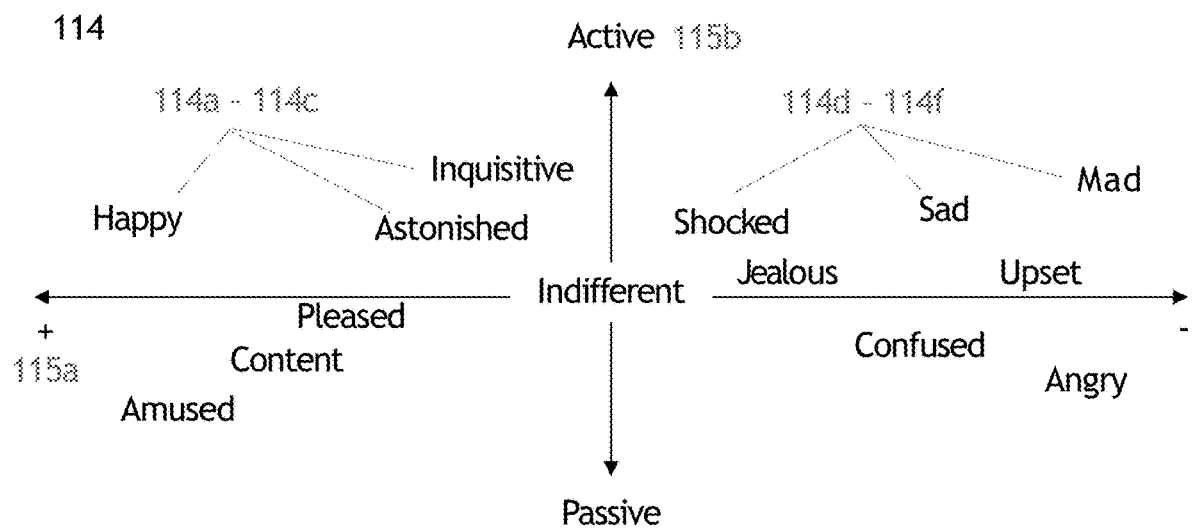
FIGS. 5A, 5B and 5C are graphical representations of one embodiment of the electronic messaging method.
Figure 5B:
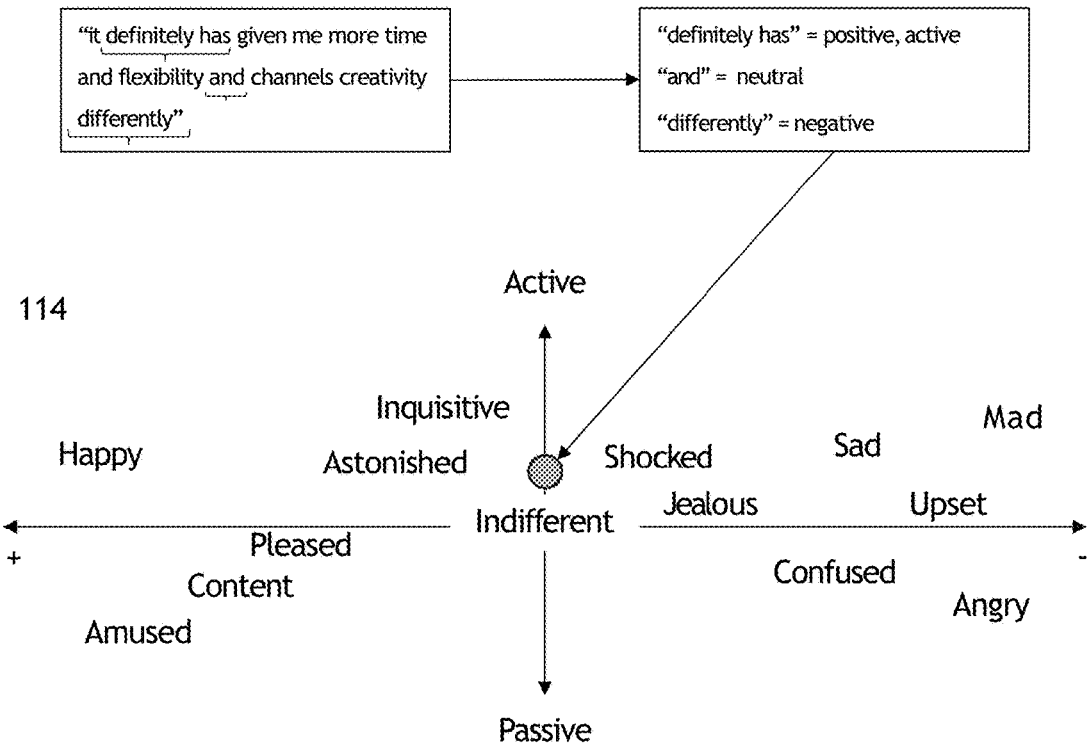
Figure 5C:
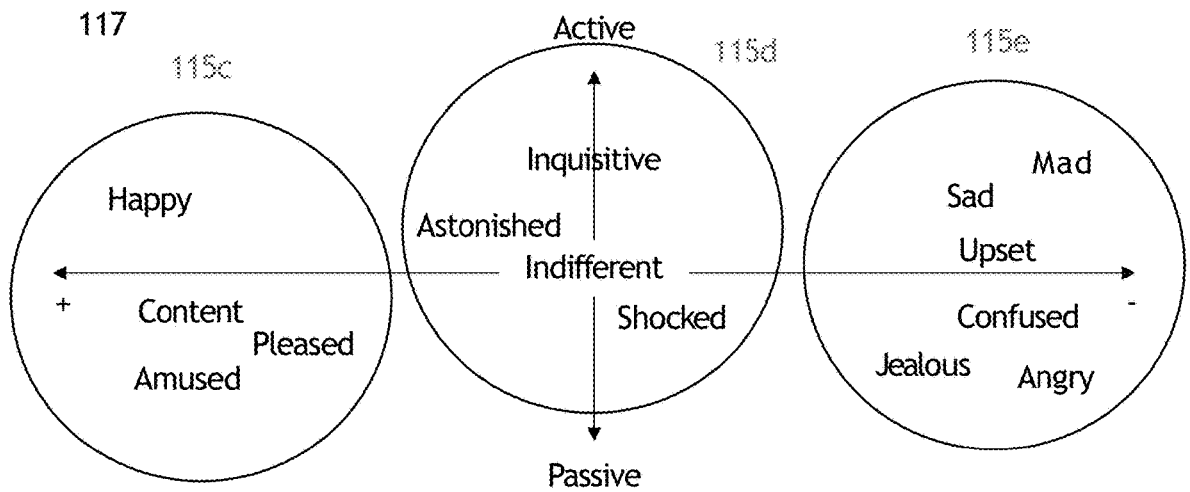

FIGS. 5A, 5B, and 5C depict a graphical representation of a dynamic sentiment value spectrum 114. In one embodiment, after parsing message content of an electronic message 160 for emotionally-charged language, the sentiment vector generator 110 can generate a sentiment value from a dynamic sentiment value spectrum 114 for the electronic message 160. In one variation of this embodiment, the dynamic sentiment value spectrum 114 can be represented as a coordinate system, as depicted in FIG. 5A. In the example depicted in FIG. 5A, the dynamic sentiment value spectrum 114 is a Cartesian coordinate system consisting of two axes: a horizontal axis 115a ranging from positive to negative (henceforth, the positivity axis) and a vertical axis 115b ranging from passive to active (henceforth, the activity axis). In this example, the dynamic sentiment value spectrum 114 consists of a multitude of different sentiments, each occupying a different position on the coordinate system. For example, the sentiments "Happy," "Astonished," and "Inquisitive" (114a-114c, respectively) all occupy the second quadrant of the coordinate system, defined by a positive position on the positivity scale and an active position on the activity scale (i.e., each of these sentiments are determined by the sentiment vector generator 110 to be positive and active sentiments). In this example, the sentiment vector generator considers Inquisitive 114c to be a more active but less positive sentiment than Astonished 114b and Astonished to be a less positive and less active sentiment than Happy 114a. Also, in this example, the sentiments "Shocked," "Sad," and "Mad" (114d-114f, respectively) all occupy the first quadrant of the coordinate system, defined by a negative position on the positivity scale and an active position on the activity scale (i.e., each of these sentiments are determined by the sentiment vector generator to be active and negative sentiments). However, the dynamic sentiment value spectrum 114 need not be a coordinate system. Rather, the dynamic sentiment value spectrum 114 may take on any appropriate form (e.g., a list, a linear scale, etc.). Additionally, the sentiment value spectrum does not need to be dynamic.

In one embodiment, as discussed above, after parsing message content contained within an electronic message 160 for emotionally-charged language, the parsing module 112 can assign attributes to the emotionally-charged language found in the message content of the electronic message 160. In one embodiment, the sentiment vector generator 110 can analyze the emotionally-language and their accompanying attributes to generate a sentiment value from the dynamic sentiment value spectrum 114, as depicted in FIG. 5B. For example, in the example depicted in FIG. 5B, the parsing module 112 can assign each emotionally-charged term found in the message content of an electronic message with respective coordinate values on the positivity and activity axes of the Cartesian coordinate dynamic sentiment value spectrum discussed in the example above. In this example, the sentiment vector generator 110 can take the coordinate position of each emotionally-charged term, calculate an average position of the emotionally-charged terms, and plot the average position on the dynamic sentiment value spectrum 114 depicted in FIG. 5A. Then, in this example, the sentiment vector generator 110 can generate a sentiment value for the electronic message by determining the sentiment value on the dynamic sentiment value spectrum 114 closest to the average position of the emotionally-charged terms.

In one embodiment, the sentiment vector generator 110 can generate a sentiment value for an electronic message 160 by determining which of the emotionally-charged terms found in the message content of the electronic message carries the most emotional weight. For example, in one embodiment, the parsing module 112 can parse the message content of an electronic message 160 for emotionally-charged language and assign each emotionally-charged term with a positivity scale value, an activity scale value, and an emotional weight value. In this embodiment, the sentiment vector generator 110 can then determine a sentiment value for the electronic message by determining which of the emotionally-charged terms has the highest emotional weight value, and then determining the sentiment value on the dynamic sentiment value spectrum 114 closest to the position of emotionally-charged term with the highest emotional weight value.

In one embodiment, the library of emotionally-charged language 112c associates each emotionally-charged term contained within the library with a sentiment value from the dynamic sentiment value spectrum 114. For example, the library of emotionally-charged language 112c may associate the words "gleeful," "splendid," and "terrific" with a "happy" sentiment value. In this example, if the message content of an electronic message 160 includes any of the terms "gleeful," "splendid," or "terrific," the sentiment vector generator 110 can generate a "happy" sentiment value for the electronic message 160. However, the sentiment vector generator can generate a sentiment value for an electronic message 160 using any other methodology.

In one embodiment, the particular user 130 may select a sentiment value from the dynamic sentiment value spectrum for an electronic message 160. In one variation of this embodiment, after the parsing module 112 parses the message content of an electronic message 160 submitted by the particular user 130, the sentiment vector generator 110 can generate multiple sentiment values for the electronic message 160 and present the multiple sentiment values for the electronic message 160 to the particular user 130 for selection. For example, after receiving electronic message 160a (depicted in FIG. 4A), the sentiment vector generator 110 may generate an "excited" sentiment value and a "melancholy" sentiment value for electronic message 160a. In this example, the particular user 130 may be given the choice to pick between the "excited" sentiment value and the "melancholy" sentiment value, in order to further ensure that the proper (i.e., intended) sentiment will be expressed.

In one embodiment, as discussed above, the system 100 includes a neural network 150 and a library of inputs 151 communicatively coupled to the sentiment vector generator 110. In one variation of this embodiment, after generating a sentiment value for an electronic message 160, the sentiment vector generator 110 store the electronic message 160 and its accompanying sentiment value in the library of inputs 151 creating a database of messages and their accompanying sentiment values. In this embodiment, the neural network 150 can employ machine learning techniques to analyze this database for patterns and trends in order to dynamically improve the performance of the sentiment vector generator 110. In one variation of this embodiment, the neural network 150 can dynamically edit or rearrange the dynamic sentiment value spectrum 114. For example, In the rearranged version, the sentiment values have adjusted and coalesced into more discrete sections (115c-115e). This may reflect that a particular user 130 associated with the rearranged sentiment value spectrum 117 generates messages most of their messages with a similar tone, making the difference between similar sentiments subtler than that of the average person.

Figure 6:
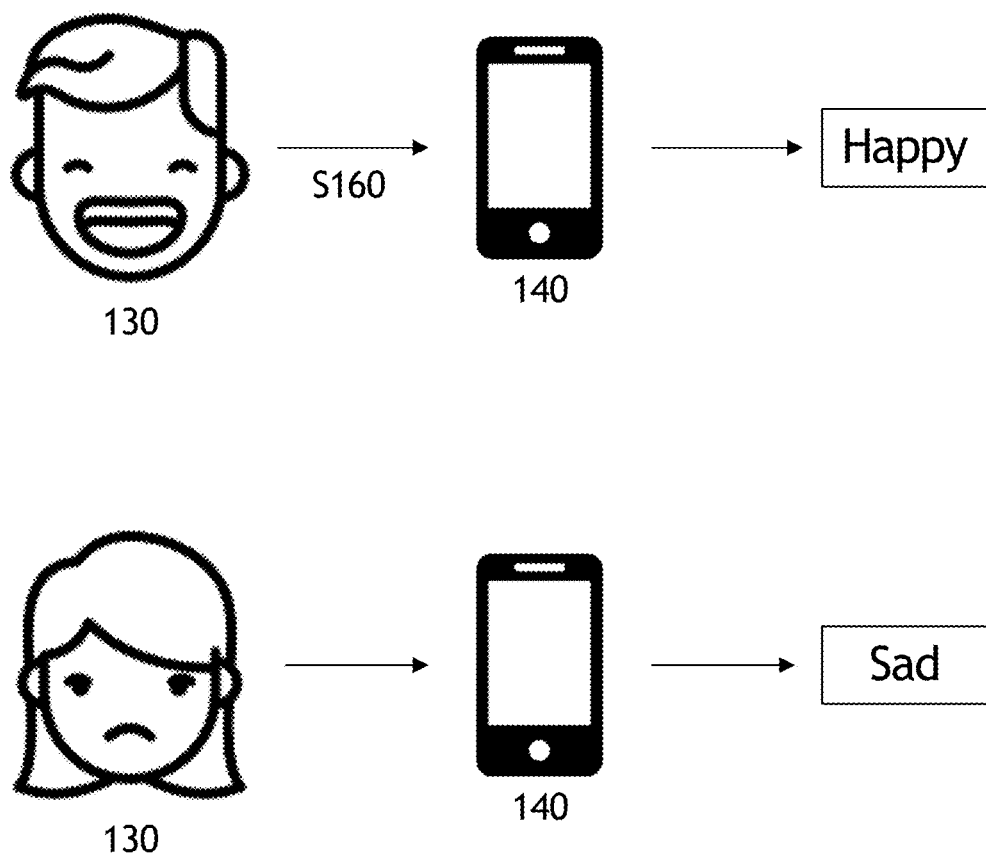
FIG. 6 is a graphical representation of one embodiment of the electronic messaging method.

In one embodiment, the sentiment vector generator 110 can generate a sentiment value for an electronic message 160 at least in part by utilizing information about a particular user 130. For example, in one embodiment, the system 100 can generate sender context associated with a particular user 130. The sender context can include, but is not limited to: social media data associated with the particular user, data obtained from IoT (internet of things) devices associated with the particular user, data obtained from wearable devices associated with the particular user, genetic profile data associated with the particular user, and stress data of the particular user. In one variation of this embodiment, the system 100 can leverage sensors and inputs coupled to an electronic computing device 140 associated with the particular user 130 to generate sender context associated with the particular user 130, as depicted by step S160 in FIG. 6. For example, in the example depicted in FIG. 6, the system 100 can leverage a camera built into a mobile phone associated with the particular user 130 to capture images of the face of the particular user. In this example, the system 100 can then analyze the images of the face of the user (e.g., the eye motion or lip curvature of the user) and determine the mood of the user at the time that the electronic message 160 is generated. The sentiment vector generator 110 can then generate a sentiment value using the determined mood of the user. In one variation of this embodiment, the system 100 can leverage sensors coupled to wearable devices associated with a particular user, such as a smart watch, intelligent contact lenses, or cochlear implants. For example, the system 100 can leverage a microphone built into a cochlear implant to capture the heartrate of a user at the time that the user is generating an electronic message 160. Using the captured heartrate, the sentiment vector generator 110 can then determine a stress level of the user at the time that the user generated the electronic message 160 and generate a sentiment value using the determined stress level of the user. Sender context can additionally or alternatively include: facial expression, motion or gesture, respiration rate, heart rate, and cortisol level.

In another variation of the previous embodiment, the sentiment vector generator 110 can generate a sentiment value for an electronic message 160 at least in part by utilizing information about an intended recipient of the electronic message 160. In this embodiment, after receiving an electronic message 160, the system 100 can determine an intended recipient 131 of the electronic message 160. The system 100 can then generate recipient context associated with the intended recipient 131. The recipient context can include but is not limited to: social media data associated with the intended recipient, data obtained from IoT (internet of things, e.g., a smart home assistant such the Amazon Echo) devices associated with the intended recipient, data obtained from wearable devices associated with the intended recipient, genetic profile data associated with the intended recipient, and stress data associated with the intended recipient. For example, in one embodiment, the system 100 can leverage sensors built into an electronic device 141 associated with the intended recipient to determine a mood of the intended recipient 131 at the time that the electronic message 160 is generated. The sentiment vector generator 110 can then generate a sentiment value for the electronic message 160 based at least in part on the determined mood of the intended recipient 131.

Figure 7A:
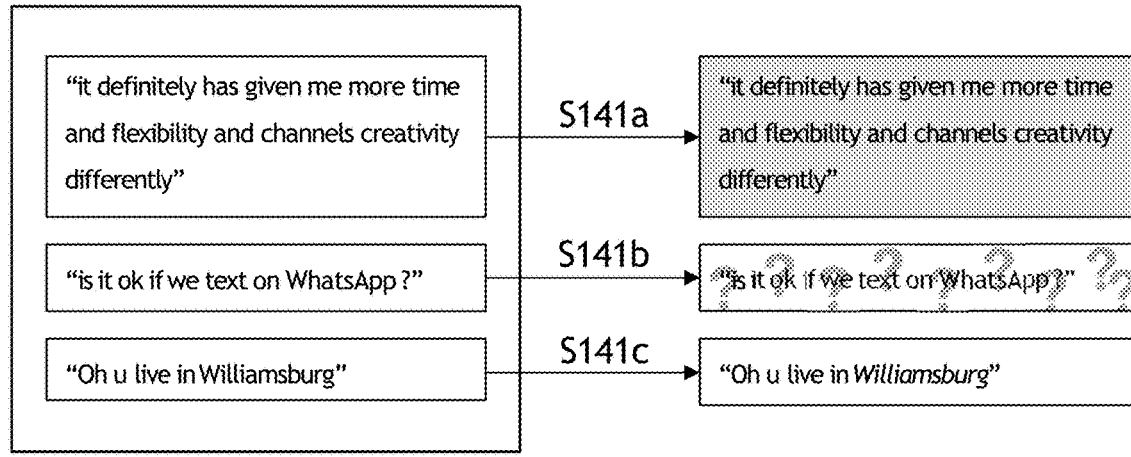
FIGS. 7A and 7B are graphical representations of one embodiment of the electronic messaging system.

After generating a sentiment value for an electronic message 160, the sentiment vector generator 110 can then select a sentiment vector from a library of sentiment vectors 118, the selected sentiment vector designed to convey a sentiment corresponding to the generated sentiment value, and impose the selected sentiment vector to the electronic message 160, as depicted in FIG. 7. The library of sentiment vectors 118 can include but is not limited to: a color change of a component of the message content, a change in the text font of a component of the message content, an audio effect, a haptic effect, and a graphical addition to the message content. For example, in one embodiment, after generating a "mad" sentiment value, the sentiment vector generator 110 may change the background of the electronic message 160, as depicted by step S141a in FIG. 7A, such as changing the background of the electronic message 160 to red to reflect the mad sentiment. Or, for example, in one variation of this embodiment, the sentiment vector generator 110 may opt to highlight only key words or terms in red, or change the fonts of key words or terms to red. The sentiment vector generator 110 can impose any sort of color change to the electronic message 160 in order to convey a corresponding sentiment.

In one embodiment, for example, after generating an "inquisitive" sentiment value for an electronic message 160, the sentiment vector generator 110 may impose a graphic onto the electronic message 160, as depicted by step 141b in FIG. 7A, such as adding question mark graphics to the background of the electronic message 160. In one variation of this example, the sentiment vector generator 110 can add one question mark to the end of the message content of the electronic message 160 in a font size that is larger than the font size of the rest of the message content. In another variation of this example, the sentiment vector generator 110 may impose a .gif file to the background of electronic message 160, in which one question mark grows and shrinks in periodic intervals. The sentiment vector generator 110 can impose any sort of static or dynamic graphic to the electronic message 160 in order to convey a corresponding sentiment.

In one embodiment, for another example, after generating a "judgmental" sentiment value for an electronic message 160, the sentiment vector generator 110 can edit the font of a key word in the message content, as depicted by step S141c in FIG. 7A, such as italicizing one of the words contained in the message content. Such font effects can include, but are not limited to, italicizing the font, changing the size of the font, bolding, underlining, and changing the spacing between characters, words, and lines. The sentiment vector generator 110 can impose any sort of font change to the electronic message 160 in order to convey a corresponding sentiment.

In one embodiment, the sentiment vector generator 110 can impose an animated character or personality to the electronic message 160, or transpose the electronic message 160 into a graphic of an animated character or personality. For example, in one variation of this embodiment, the library of sentiment vectors 118 may include a series of the same animated character (take, for example, an animated llama or chicken) performing various actions associated with various corresponding sentiments. For example, the library of sentiment vectors 118 may include a static or dynamic graphic of an animated chicken stomping with red eyes (expressing anger), another graphic of the animated chicken laying in a hammock and basking in the sun (expressing contentedness), and another graphic of the animated chicken blowing a kiss (expressing affection). In this example, after generating an "anger" sentiment value for an electronic message 160, the sentiment vector generator 110 can transpose the electronic message into the graphic of the animated chicken stomping and saying the message content of the electronic message 160.

In one embodiment, the sentiment vector generator 110 can impose a haptic effect onto an electronic message 160. For example, after generating an "anger" sentiment value for an electronic message 160, the sentiment vector generator 110 can impose a vibration or vibration pattern onto the electronic message 160, as depicted by step S141d in FIG. 7B, such as three short vibrations. In another example, after generating a "contented" sentiment value for an electronic message 160, the sentiment vector generator 110 can impose one long and muted vibration to the electronic message 160. The sentiment vector generator 110 can impose any form of vibration or vibration pattern to an electronic message in order to convey a corresponding sentiment.

In one embodiment, the sentiment vector generator 110 can impose an audio effect onto an electronic message 160. For example, after generating an "unhappy" sentiment value for an electronic message 160, the sentiment vector generator 110 can impose an audio accompaniment onto the electronic message 160, as depicted by step S142 in FIG. 7B, such as protracted "nooo." In another example, the sentiment vector generator 110 can impose a voice accompaniment dictating the message content of the electronic message 160 and stressing key words contained within the message content. The voice accompaniment may stress key words contained within the message content in any number of ways including, but not limited to: increasing or decreasing in volume, changing the intonation of the voice, changing the speed of the voice, or changing the cadence of the voice accompaniment. In one embodiment, the voice accompaniment vector may be a recorded and processed version of the particular user's voice. In one embodiment, the voice accompaniment vector may be the voice of another individual, such as a celebrity, or a combination of the particular user's voice and the voice of another individual.

Figure 7B:
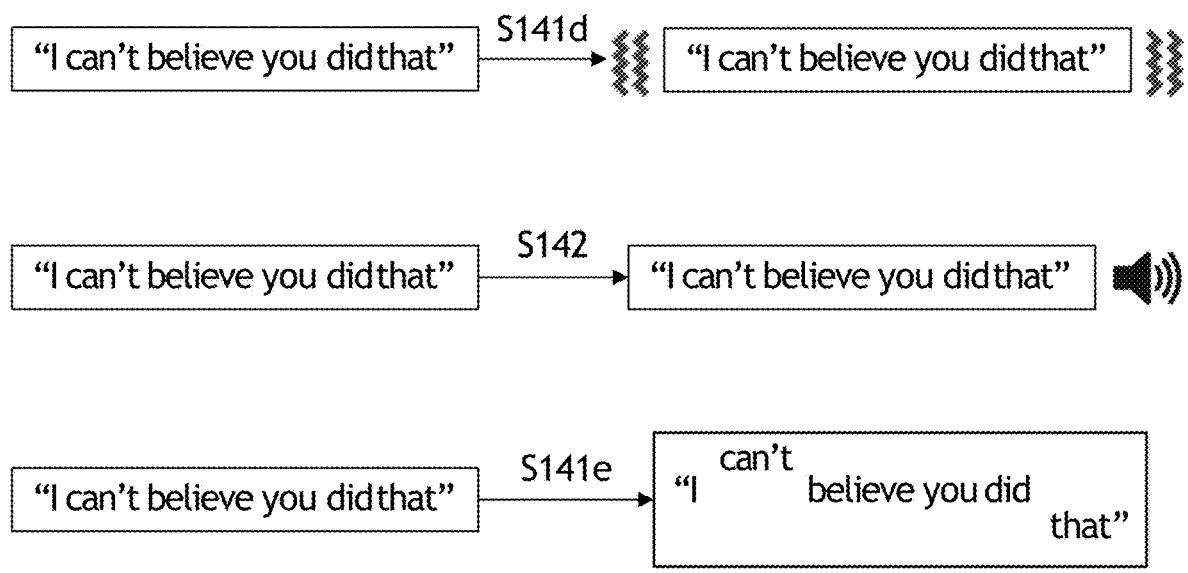
Figure 8A:
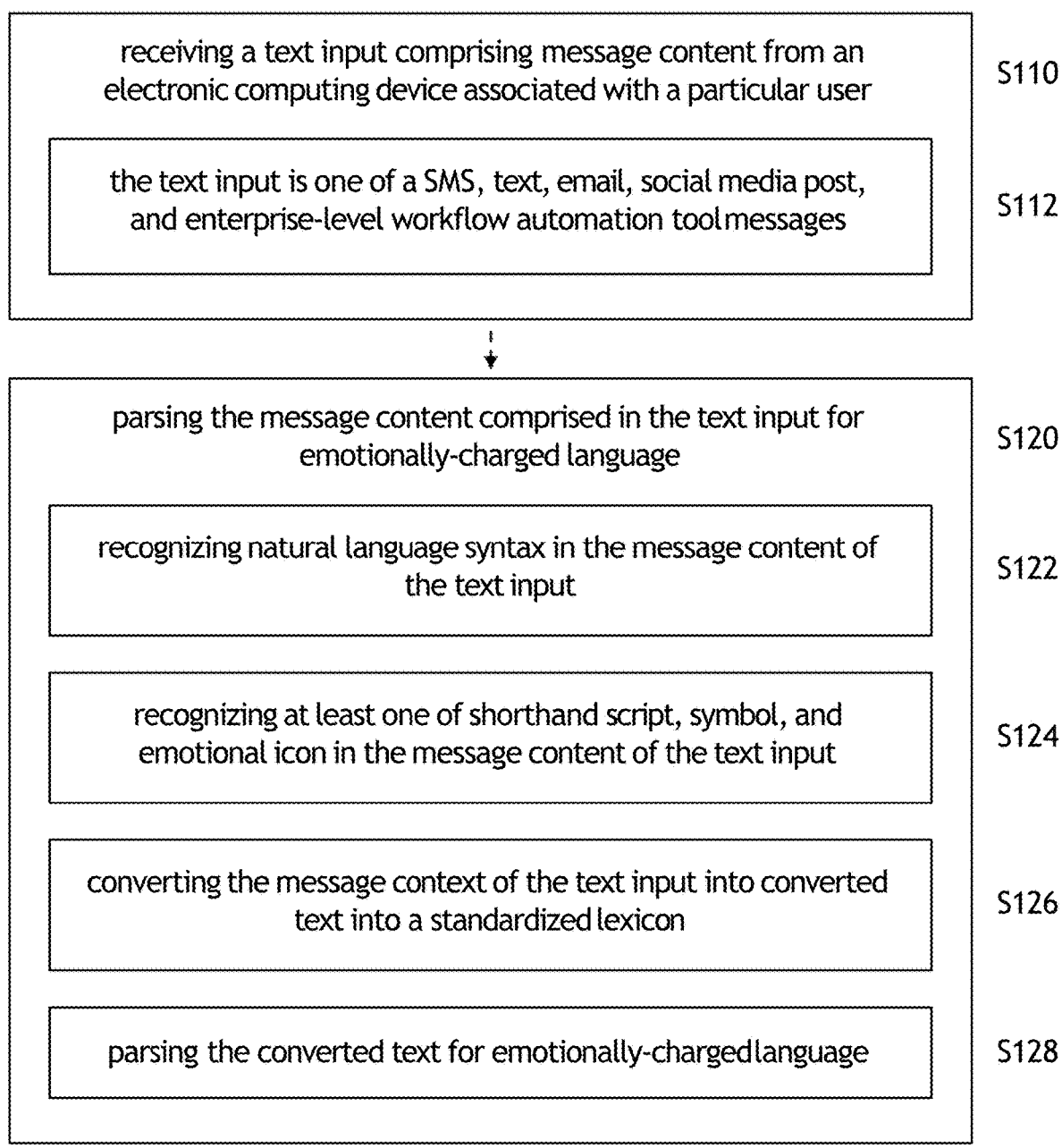
Figure 8B:
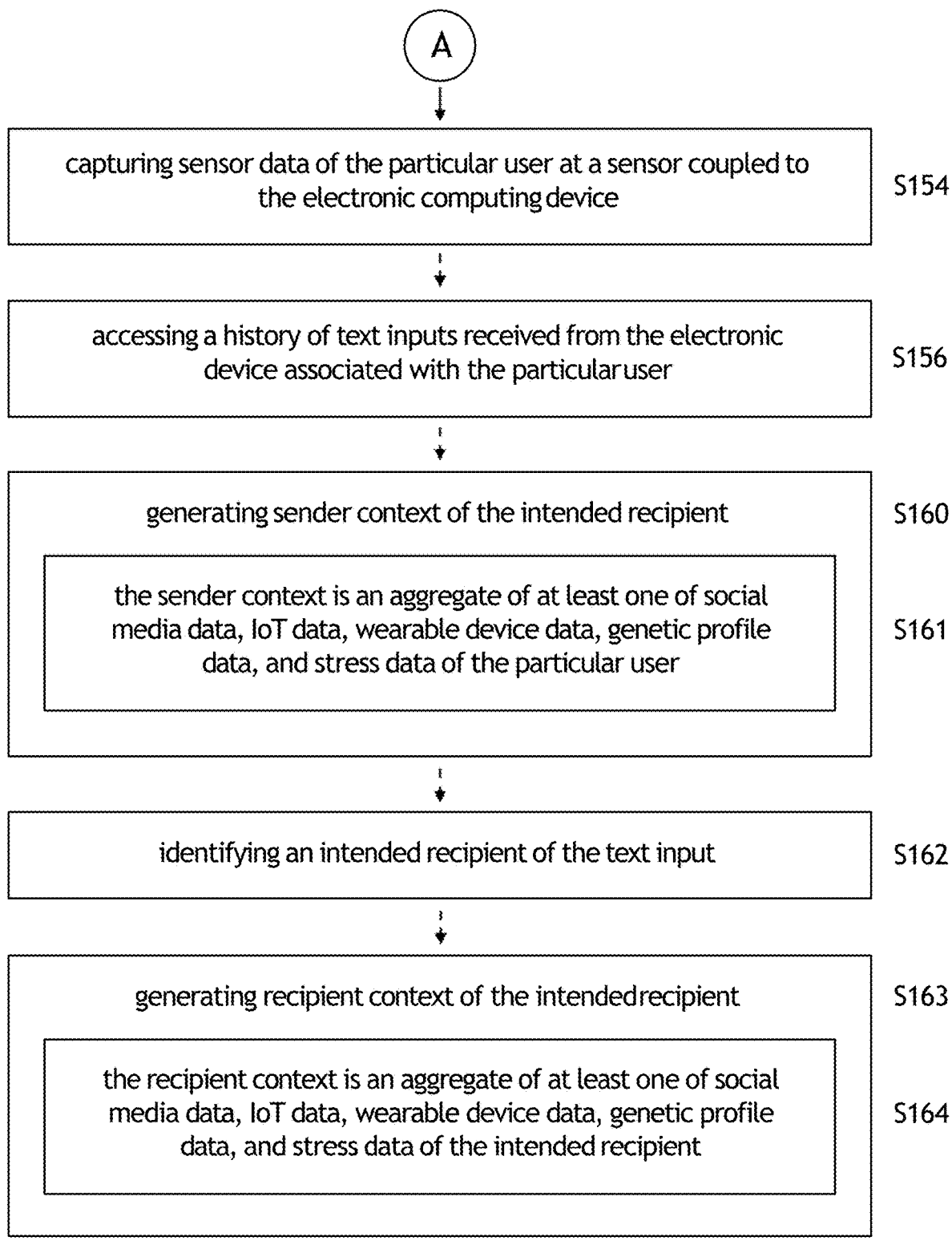
Figure 8C:
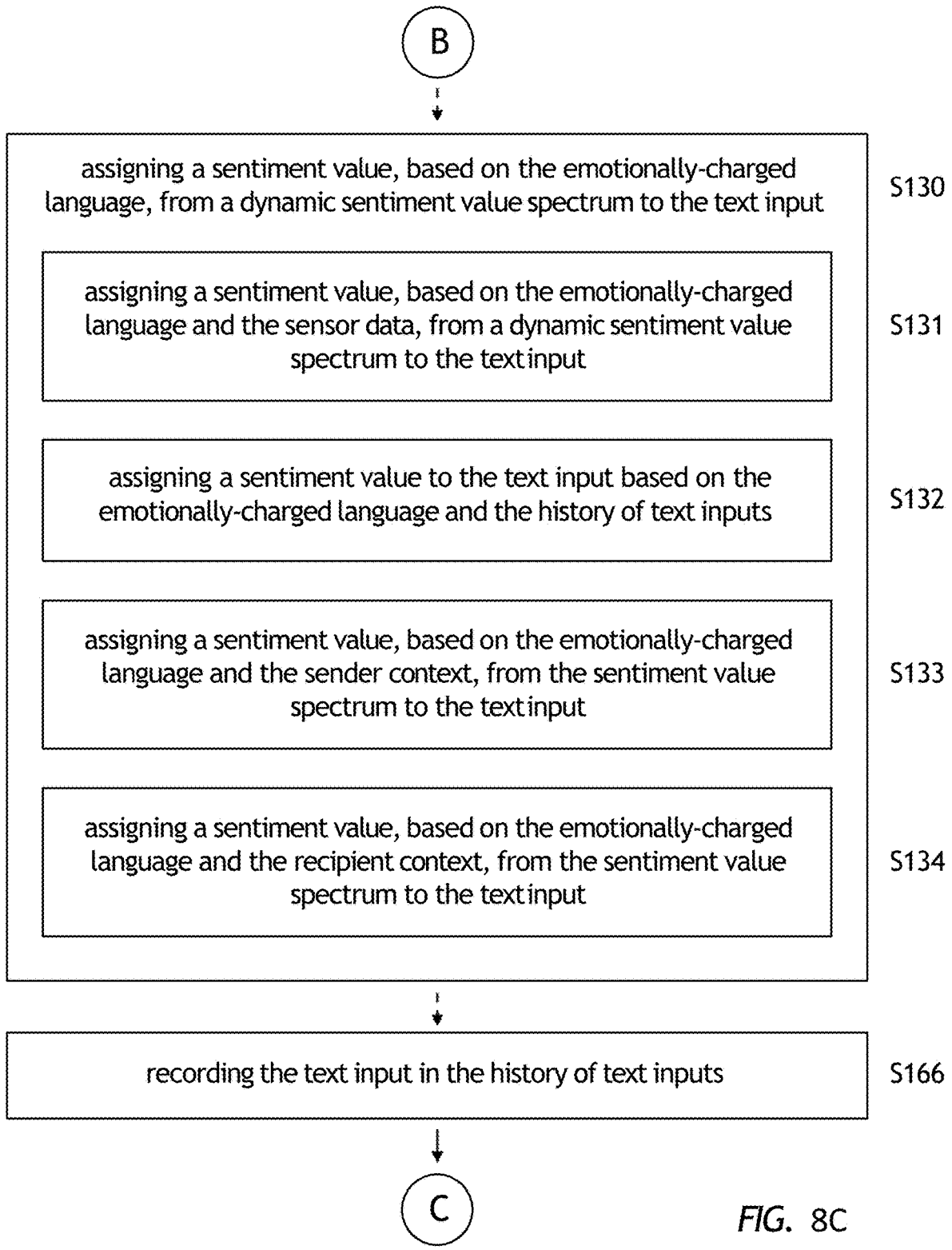

In one embodiment, after generating a sentiment value for an electronic message 160, the sentiment vector generator 110 can impose a vector onto the electronic message 160 that adjusts the position of the words contained with the message content of the electronic message, as depicted by step S141e in FIG. 7B. In one variation of this embodiment, the adjustment of the words contained within the message content is static, such that the words occupy new positions in a static image. In one variation of this embodiment, the adjustment of the words contained within the message content is dynamic, such that the words contained within the message content move within the resulting vectorized message.

In one embodiment, a user may submit sentiment vectors to the sentiment vector generator 110. For example, in one embodiment, a user may submit a picture or graphic design to impose onto the background of an electronic message and select a sentiment value for the picture or graphic design to be associated with. In this example, after generating a sentiment value for an electronic message 160 corresponding to the sentiment value that the user has selected to associate with the picture or graphic design, the sentiment vector generator 110 can impose the picture or graphic design to the background of the electronic message 160 to convey the corresponding sentiment. In another example, in one variation of this embodiment, a user can select a sentiment vector previously included in the library of sentiment vectors 118 and previously associated with a sentiment value and disassociate the sentiment vector from the associated sentiment value, or re-associate the sentiment vector with a different sentiment value. In yet another example, in one variation of this embodiment, a user can select one or more elements from existing sentiment vectors contained within the library of sentiment vectors 118 and combine them to create a new sentiment vector. In this example, the user can also choose a sentiment value to associate with the new sentiment vector. In another example, in one variation of this embodiment, a user can select a sentiment vector by scrolling through a list of sentiment vectors (e.g., a list including options to adjust text weight, height, font, color, highlight, or content animation) using a flicking gesture, within a mobile application, on a touch screen coupled to an electronic computing device.

The sentiment vector generator can include or generate, but is not limited to, sentiment vectors using any combination of the elements of the sentiment vectors described herein. Additionally, environmental conditions and factors for example, but not limited to, wind, heat, humidity, cold may also play a role in generating the sentiment vector.

In one embodiment of the system 100, a user can submit an electronic message 160 to the sentiment vector generator 110 through a mobile application (e.g., a native application), as discussed above. In one variation of this embodiment, the mobile application can store vectorized messages generated by the sentiment vector generator and allow the user to search through the vectorized messages. In this embodiment, the user can search through the vectorized messages using different filters or queries including, but not limited to: mood, color, content, and sentiment. For example, in one embodiment, the user can enter a sentiment as "anger" as a search query, and a graphical user interface of the mobile application can display a list of all of the vectorized messages that the user has created through the sentiment vector generator 110 with a sentiment value corresponding to an "anger" sentiment. In one embodiment, the sentiment vector generator 110 can impose a hyperlink onto an electronic message 160. FIGS. 8A, 8B, 8C, and 8D are flow diagrams of one embodiment of the electronic messaging system.

In an embodiment of the invention, the sentiment vector generator 110 can impose a hyperlink onto an electronic message 160. An imperative function of the sentiment vector is GEEQ (genetics, emotion and electroencephalography) and its capacity to integrate messages and messaging with movement and thought as well as the ability to pair information with form and performative elements. In a nutshell, our technology will introduce, integrate, account for, and actively utilize GEEQ (Genetics, Emotion, and Electroencephalography). GEEQ, by its very desgn, integrates and intermingles the beliefs and postulates of Darwin, Mendel, Mendelssohn, Morgan, and Martha Graham.

Figure 9:
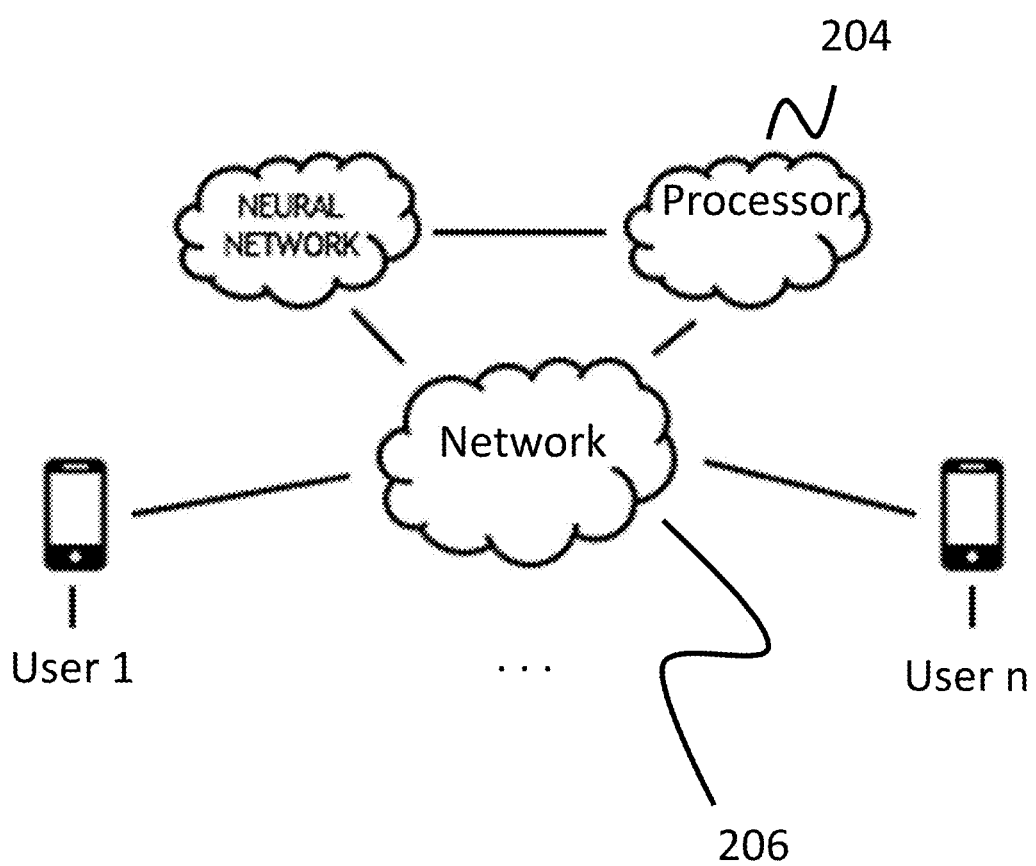
FIG. 9 illustrates a network diagram in accordance with an aspect of the invention.

FIG. 9 illustrates a network diagram of the digital therapeutic system in accordance with an aspect of the invention. As shown, at least one processor 204 is connected to the Internet (network) 206 via either a wireless (e.g. WiFi link) or wired link to an Internet connected router, usually via firewall. The network 206 may be any class of wired or wireless network including any software, hardware, or computer applications that can provide a medium to exchange signals or data. The network 206 may be a local, regional, or global communication network. Various servers 204, such as a remote VCS Internet server, and associated database memory can connect with the at least a user device (1 . . . n). Additionally, various user devices (e.g. Smartphones, tablet computers, laptop computers, desktop computers and the like) can also connect to both the processor-controlled IoT hubs, sensors disposed on the device configured for data gathering, and/or the remote VCS Internet server 204.

As will be discussed, often a plurality of different user devices may be used, but for simplicity this plurality of devices will often be spoken of in the singular form. This use of the singular form is not intended to be limiting, and in general the claims and invention should be understood as operating with a plurality of devices. Although for simplicity, often mobile client computerized devices such as Internet connected versions of the popular Android, iOS, or Windows smartphones and tablets will be used as specific examples of devices, these specific examples are not intended to be limiting. The electronic computing device may include any number of sensors or components configured to intake or gather data from a user of the electronic computing device including, but not limited to, a camera, a heart rate monitor, a temperature sensor, an accelerometer, a microphone, and a gyroscope. The electronic computing device can also include an input device (e.g., a touchscreen or a keyboard) through which a user may input text and commands.

While not shown, note that server, Internet connected storage device and database memory may all be located in the cloud. This is intended to both designate and remind the reader that the server, Internet connected storage device and database memory are in fact operating according to scalable Internet cloud-based methods that in turn operate according to automated service provisioning and automated virtual machine migration methods. As previously discussed, examples of such scalable methods include, but are not limited to, Amazon EC2, Microsoft Windows Azure platform, and the Google App Engine. Thus, for example, server and Internet connected storage device will often be implemented as automatically provisioned virtual machines under a cloud service system that can create a greater or lesser number of copies of server and Internet connected video storage device and associated database memory according to the underlying demands on the system at any given time.

Preferred embodiments may include the addition of a remote server 204 or cloud server to further provide for back-end functionality and support. Any one of the storage or processing may be done on-board the device or be situated adjacent or remotely from the system and connected to each system via a communication network 206. In one embodiment, the server 204 may be used to support user behavior profiling; user history function; predictive learning/analytics; alert function; network sharing function; digital footprint tracking, etc. The remote server 204 may be further configured to authenticate the user and retrieve data of the user, device, and, or network and applies the data against a library of messages, content, validated user information, etc.

Figure 10:
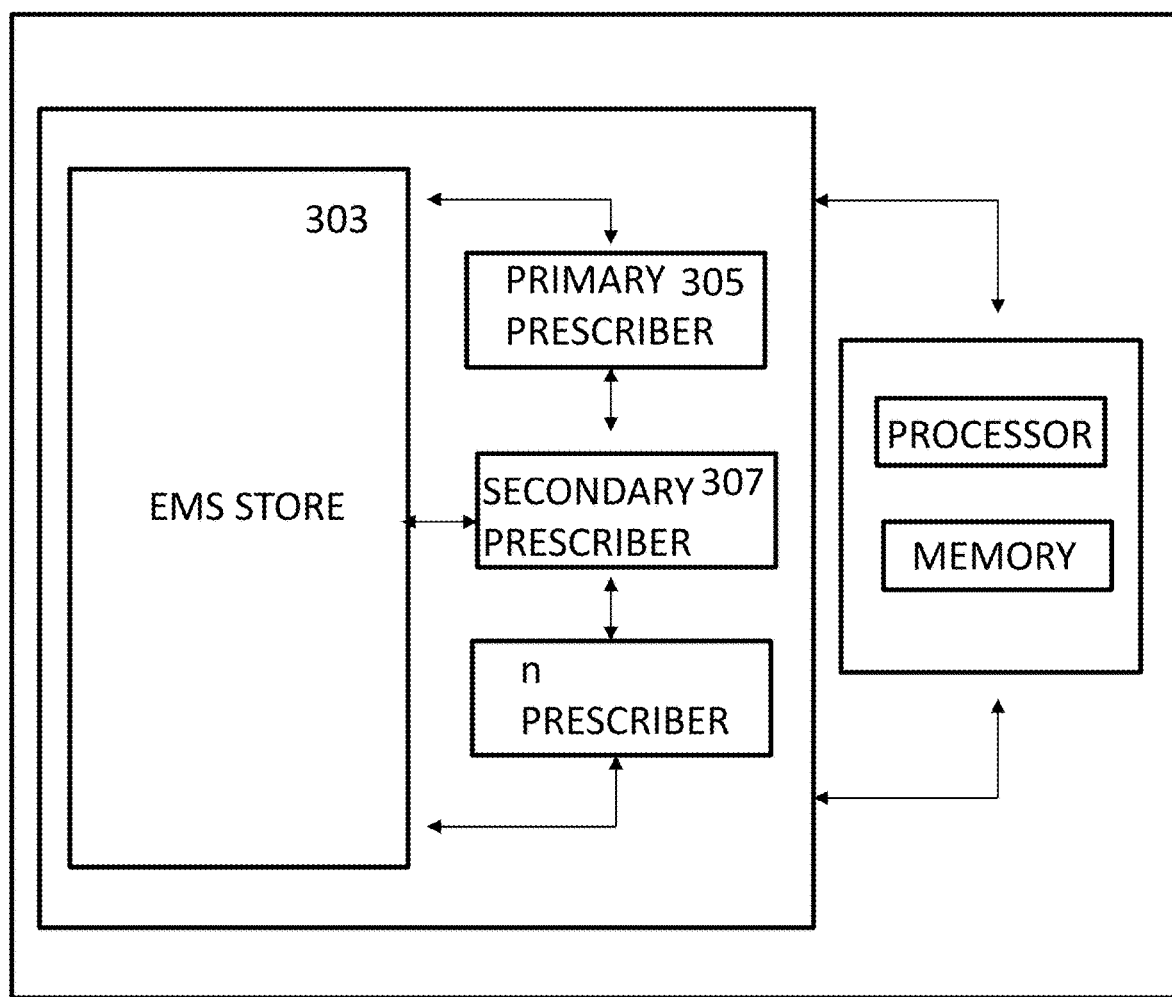
FIG. 10 illustrates a block diagram depicting the digital therapeutic system in accordance with an aspect of the invention.
Figure 11:
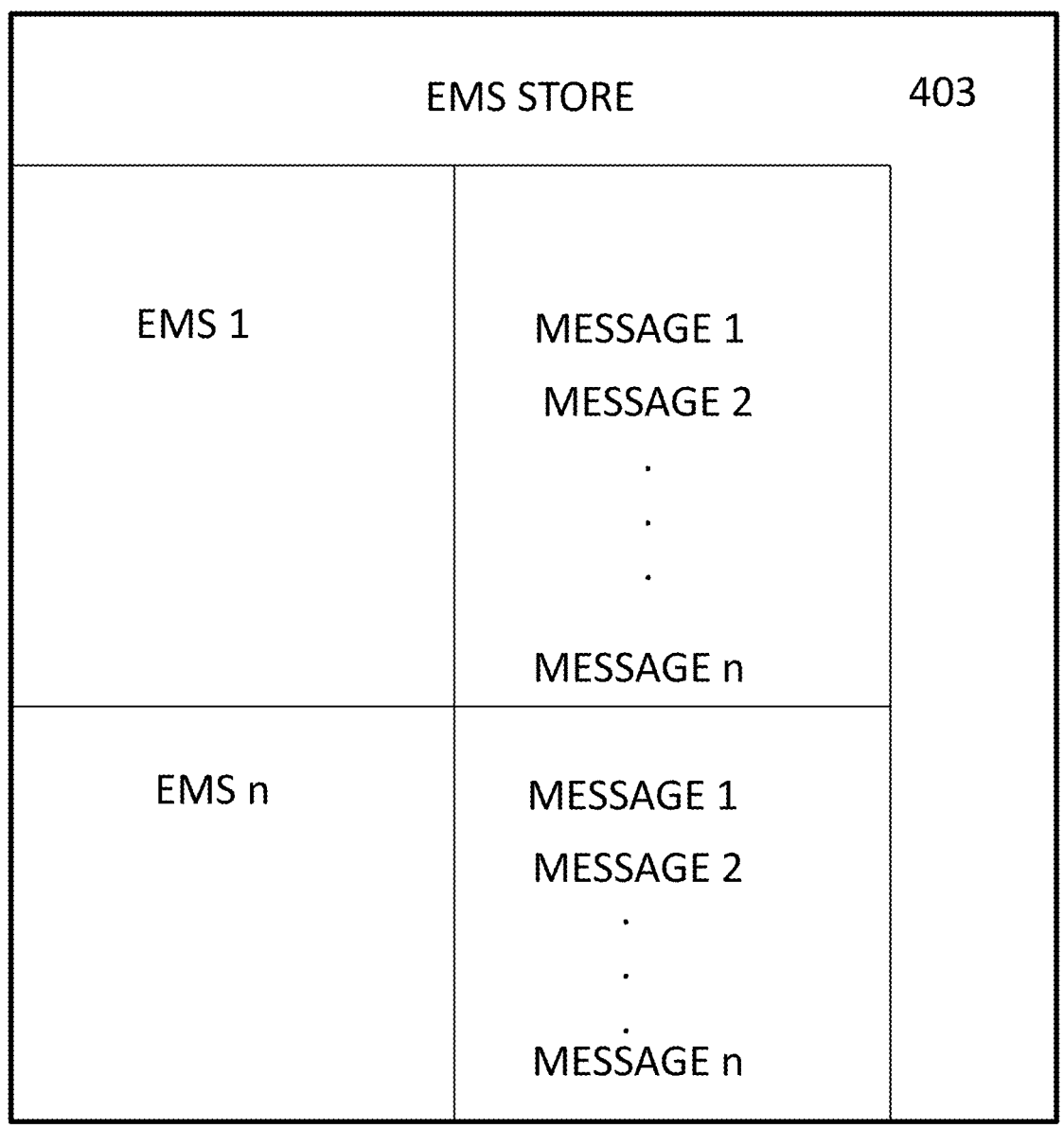
FIG. 11 illustrates a block diagram depicting the digital therapeutic system in accordance with an aspect of the invention.

Now in reference to FIGS. 10 and 11. FIGS. 10 and 11 both illustrate an exemplary embodiment of the digital therapeutic delivery system. FIGS. 10 and 11 illustrate an exemplary processing unit with at least a one prescriber 305, 307 configured for displaying interactively therapeutic content from an EMS store 303, 403 based on a user-specific EMS. As shown, the system may comprise an EMS store 303, 403; at least a primary message prescriber 305; a processor coupled to a memory element with instructions, the processor when executing said memory-stored instructions, configure the system to cause: at least one EMS from a plurality of EMS in the EMS store 303, 403 to be selected by the user.

As shown in FIG. 11, any number of EMS or EMS types may be included in the EMS store 303, 403. Each EMS may indicate at least one of a feeling, sensation, type of discomfort, mood, mental state, emotional condition, physical status of the user, and, or a behavioral intervention or training regimen. FIG. 11 also illustrates the fact that any number of messages or interactively therapeutic content may be associated with each EMS type. Each message; or interactively therapeutic content; or pushed therapeutic may contain at least one of a text, image, sound, video, art asset, suggested action or recommended behavior. The matching of message; interactively therapeutic content; or pushed therapeutic with EMS type may be pre-defined by at least one of an accredited expert or source; probabilistic; or deep learned. In a preferred embodiment, an accredited expert or source will require at least two independent sources of peer-reviewed scholarship or data in order to validate the match.

The at least primary message prescriber 305 may push a message or interactively therapeutic content personalized to the user based on at least one stored message matched to the selected EMS. For example, within the EMS store 403, if EMS 1 (lethargic) is selected as defined by the user or the system, any one of message 1, 2 . . . n may be selected by the prescriber 305. The pre-defined messages validated by the accredited expert may all be messages with documented utility in elevating mood and energy (rubric). The mood and energy documented for each message may be on a scale. For instance, EMS 1 message 1 may be low-moderate; EMS 1/message 2 may be moderate; and EMS 1/message n may be high-severe, etc. Any variant of the scale may be featured without departing from the scope of the invention. In other embodiments, the messages, while falling under the same rubric and un-scaled, can vary along design cues. For instance, the prescriber 305 may choose EMS 1/message 2, over other available messages, due to the fact that the message is comprised of traditionally feminine cues (pink-colored bauhaus typeface) for a female user. Other user profile or demographic information may further inform the prescribers 305 choice of message type, such as age, education level, voting preference, etc. User profile or demographic information may be user inputted or digitally crawled.

Still in reference to FIG. 11, the prescriber's 305 choice of message type is not specific to a user, user profile, or crawled user data. In a certain embodiment, the prescriber 305 may have to choose between any one of the message types (message 1, message 2 . . . message n) from the selected EMS type. This type of message assignment may be completely arbitrary. In other embodiments, the message assignment may be not specific to a user-generated or crawled profile but may be based on user history. In other words, a user's tracked level of engagement with a previous message or message from a previous session may inform message assignment by the prescriber 305. Tracking engagement of a user with a pushed or prescribed therapeutic message may be by camera-captured eye gazing, touch-screen interaction, time span between pushed therapeutic and user follow-up action, choice of follow-up action, etc.

In some embodiments, the full list of message types is not grouped by EMS type or along any design categories, but rather simply listed arbitrarily and mapped or matched to an appropriate EMS type. In this arbitrarily listed manner, the prescriber 305 may match to more than one EMS type. Likewise, a user may be defined by more than one EMS type and be prescribed the same message type.

Figure 12:
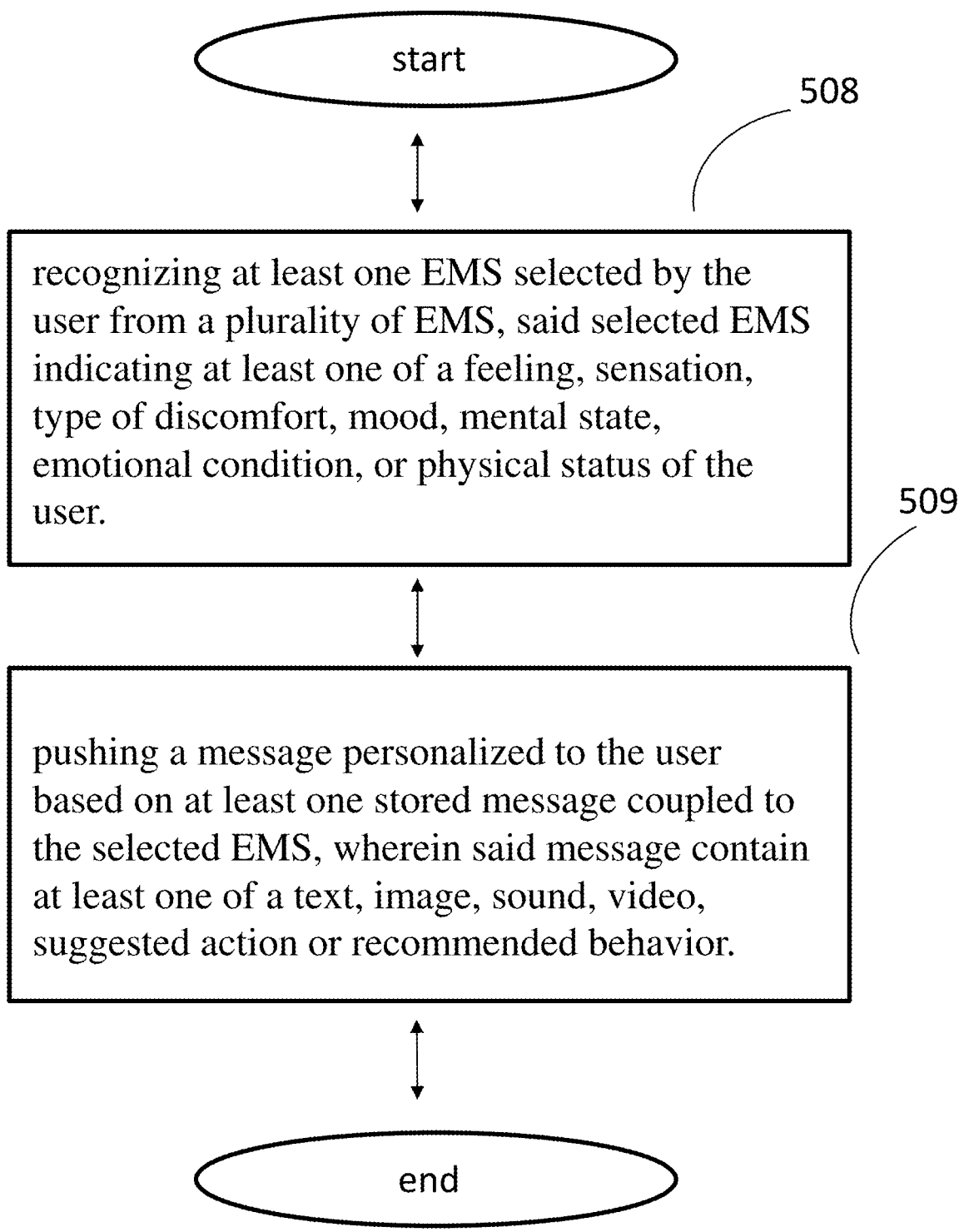
FIG. 12 illustrates a flow diagram depicting the digital therapeutic method in accordance with an aspect of the invention.

FIG. 12 illustrates a flow diagram depicting the method of delivering a digital therapeutic in accordance with an aspect of the invention. In a preferred embodiment, the method may comprise the steps of: (1) recognizing at least one EMS selected by the user from a plurality of EMS, the selected EMS indicating at least one of a feeling, sensation, type of discomfort, mood, mental state, emotional condition, or physical status of the user 508. Once the EMS is defined, the method then calls for (2) pushing at least a primary-level message personalized to the user based on at least one stored message coupled to the selected EMS 509.

In some embodiments, the system or method may call for pushing at least a secondary-level message personalized to the user based on a threshold-grade match of the user response to the pushed primary-level message with at least one stored response coupled to a stored primary-level message, whereby the user and stored response is a measure of at least one of a reaction, compliance, engagement, or interactivity with the pushed and, or stored primary-level message. Much like the primary message or primary-level message, the secondary-level messages may also contain at least one of a text, image, sound, video, art asset, suggested action or recommended behavior. Again, the efficaciousness or therapeutic value of the primary or secondary messages are validated by at least one—and typically two—independent sources of clinical research or peer-reviewed science, as verified by a credentialed EMS expert.

In order to facilitate the at least secondary message or secondary-level message, the primary prescriber 305 may be used: Assigning a second message to the same user in the same session for the first defined EMS type. As is with the the assignment of the first message, the assignment of the second may arbitrarily choose among EMS-grouped messages or from the full arbitrary list of messages in the EMS store. Moreover, the primary prescriber 305 may perform the secondary assignment in a logic-defined manner, wherein gathered, contextualized, or profiled data informs the assignment. In yet other aspects, second-level assignment may be performed by at least a secondary message prescriber 307, wherein the at least secondary message prescriber 307 pushes at least a secondary-level message personalized to the user based on a threshold-grade match of the user response to the pushed primary-level message with at least one stored response coupled to a stored primary-level message, whereby the user and stored response is a measure of at least one of a reaction, compliance, engagement, or interactivity with the pushed and, or stored primary-level message.

For instance, when a user-generated or system-generated EMS is defined as 'unfulfilled' for user A, a primary prescriber 305 assigns message 2 (uplifting; inspiring message) from EMS 1 (unfulfilled). In one embodiment, a secondary prescriber 307 prescribes a pro-social behavior, such as a local community service, immediately upon a touch interaction with the first inspiring message pushed. In other embodiments, a level of engagement, interaction or compliance may be tracked by the system to infer severity of the EMS. For instance, if user A does not comply with the touch-interaction requests from the first inspiring message or pro-social behavior recommendation of the second message, then the secondary prescriber 307 may push a less physically strenuous pro-social recommendation, such as suggesting to call an in-network licensed expert or simply make a cash donation to a charitable organization of the users choosing via a linked micro-payment method. For the purposes of inferring severity of EMS, any number of diagnostics that leverage any one of the on-device tools may be used, such as gyroscopic sensors or cameras. Secondary assignment may also be based on learned history, such as a past positive reaction (compliance) to a receiving a message from a loved one that a donation was made in user A's name to a charitable organization. Based on such history, a secondary prescriber 307 may assign a primary or secondary message recommending to make a donation in the name of a loved one during an 'unfulfilled' EMS experienced by user A.

The processing unit may further be communicatively coupled to at least one of an interface module, display module, input module, logic module, a context module, timeline module, tracking module, notification module, and a payment/gifting module. In accordance with one aspect, the notification module may be configured to generate reports at regular intervals (such as daily at 12:00 PM, weekly and monthly), on-demand (when the user requests for a report corresponding to the user), when triggered by an event, or upon a detected severe EMS. In an embodiment of the present invention, the notification module may also be configured to send a notification to the user or to a chosen loved one of the user. The notification may be a message, a phone call or any other communication means.

In an embodiment of the present invention, a timeline module may push already pushed messages in at least one of a static, dynamic, and, or scheduled fashion based on at least one of the user's scheduler criteria. The line of static, dynamic, and, or scheduled messages may be curated by the user, pre-set, or dynamically pushed based on any one of a user parameter. In some embodiments, the timeline module enables the displayed line of static, dynamic, and, or scheduled messages to be further replicated on at least one of a social media timelines or stories. In other words, the timeline module enables the displayed messages to be further shared with social media outlets.

In an embodiment of the present invention, a payment or gifting module may enable purchasing and gifting donations, physical objects, or digital assets. The gifting module may further be coupled to a distributive digital ledger, wherein each transaction among any user is represented as a unique node in the digital ledger. Each node tagged with meta data facilitating at least one of a transaction, validation and, or registration for each transaction.

Figure 13:
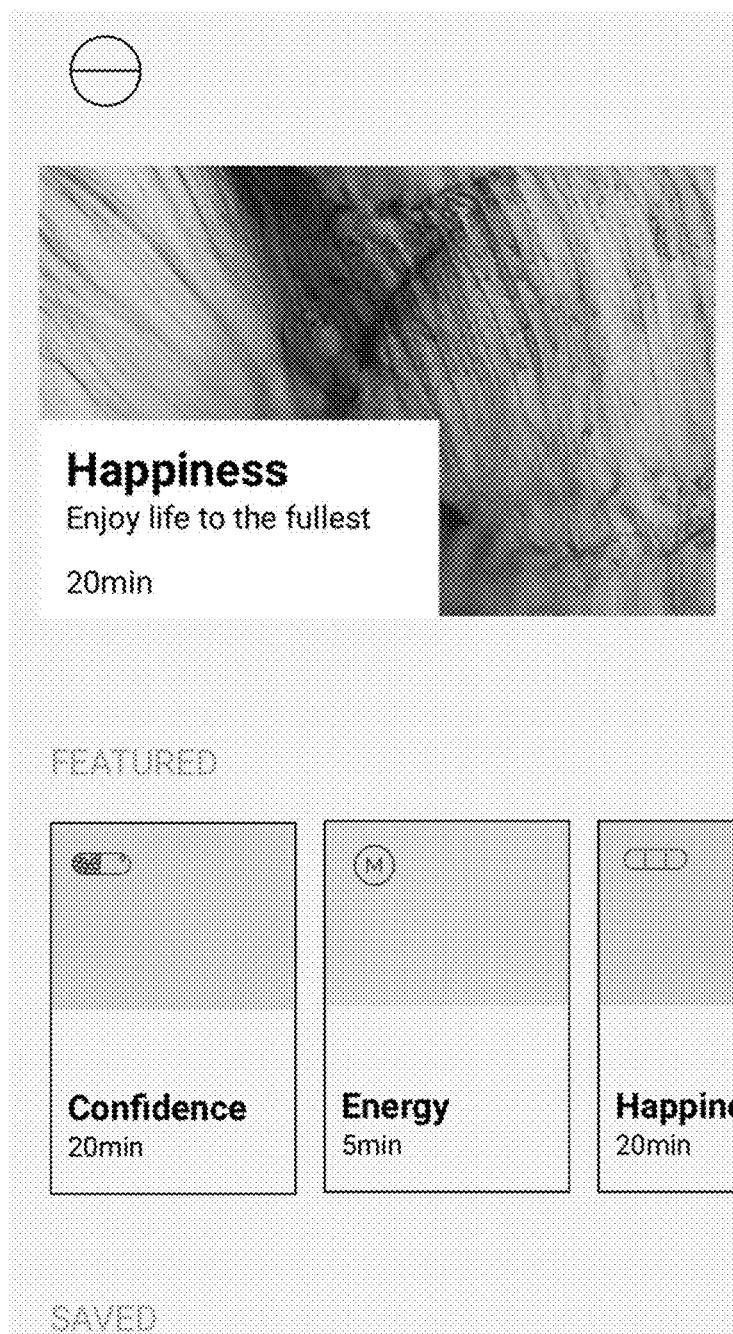
FIG. 13 illustrates a representative screen shot depicting an exemplary user interface in accordance with an aspect of the invention.

FIG. 13 is a representative screen shot depicting an exemplary user interface in accordance with an aspect of the invention. As shown, the top layer 602 depicts a spotlighted EMS and the bottom layer is a scroll menu of EMS. In this case, the concept of EMS, as earlier defined, also includes behavioral interventions or training regimens, in addition to an emotional and mental state. In some embodiments, an exemplary user experience may have both top layer 602 and bottom layer 604 within the same screen, wherein the top layer 602 is a spotlighted rendering of the focused EMS from the EMS menu depicted in the bottom layer 604. In other embodiments, the window may only feature the scrolling EMS menu as depicted in the bottom layer 604, wherein the focused EMS from the plurality of EMS may pop-out, or be emphasized anyhow. In yet other embodiments, the window may only feature the one EMS at a time, allowing for the user to go through the entire menu, one window (EMS) at a time. In yet other embodiments, the menu may be featured in a thumbnail format, allowing the user to choose at least one EMS from a thumbnail menu, sized to fit in a single window, or alternatively, configured for scrolling.

Figure 14:
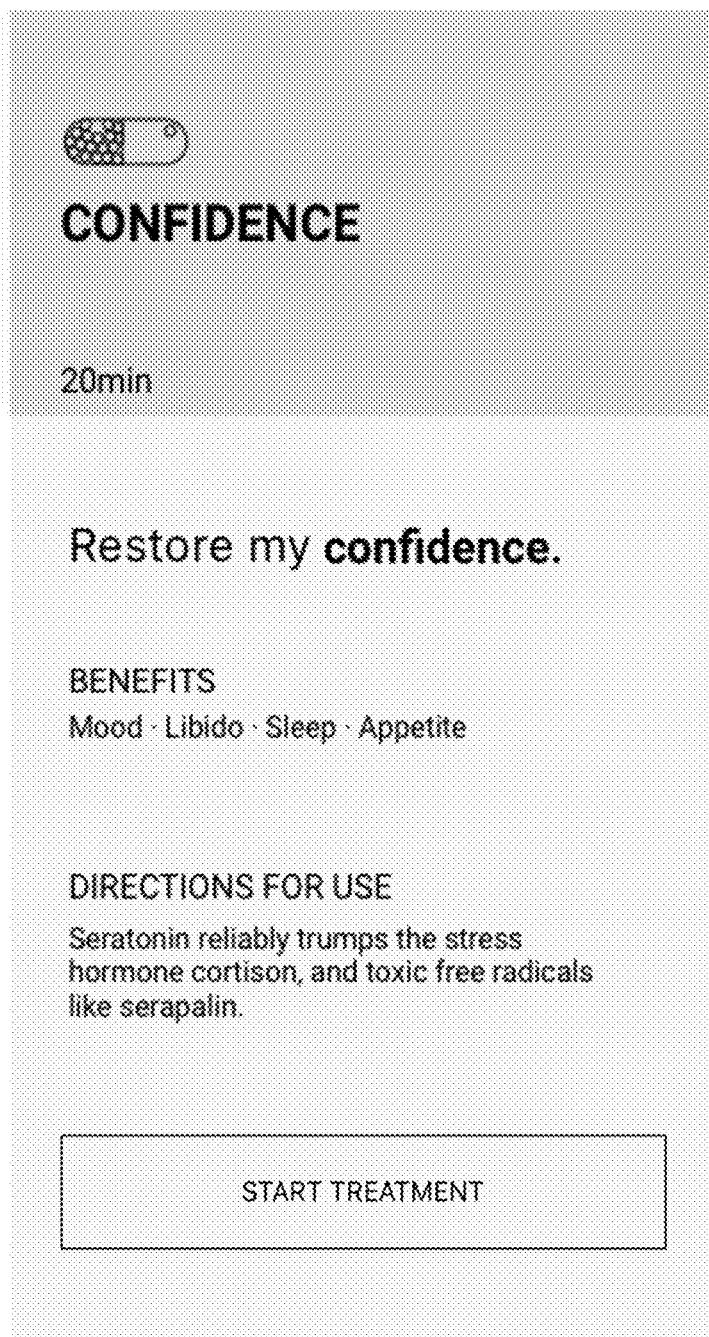
FIG. 14 illustrates a representative screen shot depicting an exemplary user interface in accordance with an aspect of the invention.

FIG. 14 is a representative screen shot depicting an exemplary user interface in accordance with an aspect of the invention. Once the EMS (behavioral intervention or training regimen) is defined, users can read more about the intervention or training regimen they're going to start and self-administer (have pushed to their device) from a top portion of the card (window) 702. On the same card (window), the bottom portion may highlight proven benefits, and then provide directions for use, mixing real guidance with elements of humor 704. The medical-inspired alliteration and iconography are intended to invoke a sense of prescriptive health care or wellness.

Figure 15:
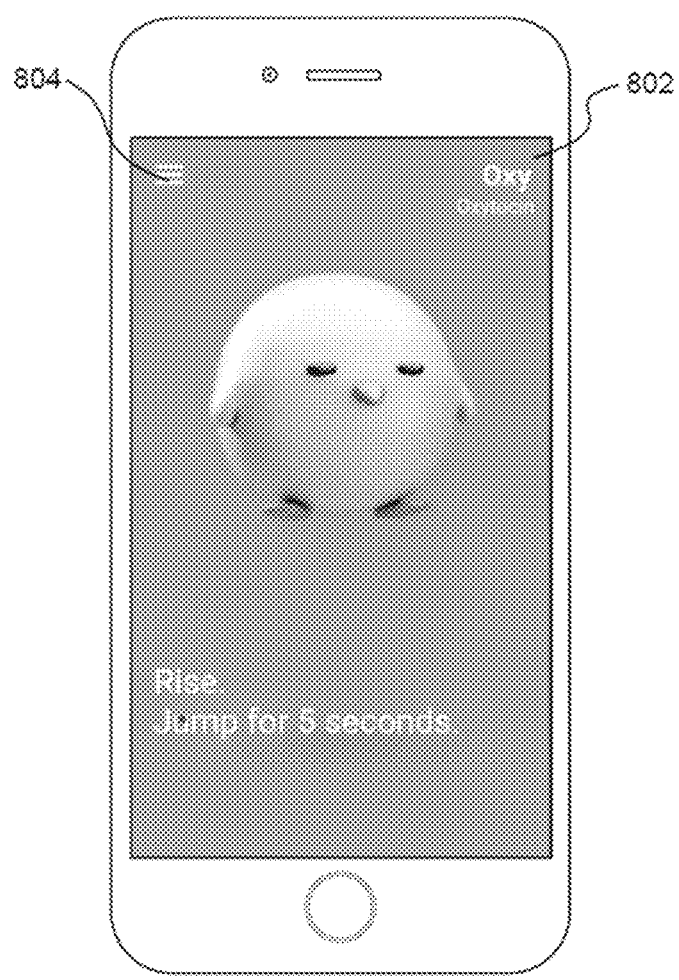
FIG. 15 illustrates a representative screen shot depicting an exemplary user interface in accordance with an aspect of the invention.

FIG. 15 is a representative screen shot depicting an exemplary user interface in accordance with an aspect of the invention. As shown, once the EMS (regimen) is defined and a particular course of treatment (message) is started, on the top-right portion of the next card explicitly identifies the specific drug benefit 802. While not shown, by tapping the drug abbreviation, users can see the source of supporting scientific research 802. By tapping the hamburger icon, users can choose to save the individual card, or share the card and its contents with friends across social media. It is to be understood by a person of ordinary skill in the art that these icons, or any icons, on this card (window), or any card (window), may be positioned elsewhere (or anywhere), without departing from the inventive scope.

The focal point of the card (window) is the actual EMS-defined message (treatment), and in the case of this window, is a suggested action—jump for 5 seconds. Jumping for 5 seconds is a suggested action to restore the oxytocin neurotransmitter, which is documented for building happiness and confidence—the initially chosen EMS or behavioral intervention by the user (FIG. 13). The veracity of the message or suggested action is supported by the referenced peer-reviewed research and co-signed credentialed expert 802. As a person, skilled in the art will recognize from the previous detailed description and from the figures and claims, modifications and changes can be made to the embodiments of the cards, windows, icons, design elements, EMS types, behavioral intervention types, message types, without departing from the scope of this invention as defined in the following claims.

While not shown in FIG. 15, the messages (cards/windows) may comprise a single or battery of physical and, or cognitive tasks and based on responses, further indicate a more nuanced EMS for a more tailored initial or subsequent message. Responses may include a level of compliance, engagement, interaction, choices, etc. Furthermore, for deeper and more nuanced EMS definition, assigning an indication score or color-coded range to further convey EMS severity may be achievable. As a result, matching of message type to scored or color-coded EMS may produce a more refined match for pushing of even more personalized digital content or therapeutics.

Figure 16:
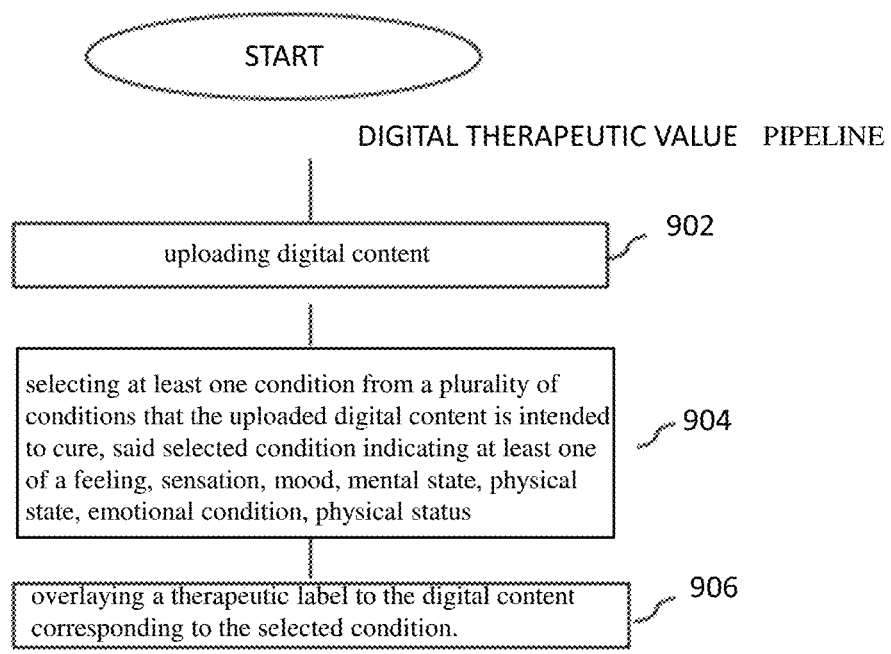
FIG. 16 illustrates a representative method flow of the therapeutic labeler in accordance with an aspect of the invention.

FIG. 16 illustrates a flow diagram depicting the method of rating or labeling a digital therapeutic to digital content in accordance with an aspect of the invention. In a preferred embodiment, the method may comprise the steps of: (1) uploading digital content 902; (2) selecting at least one condition from a plurality of conditions that the uploaded digital content is intended to cure, said selected condition indicating at least one of a feeling, sensation, mood, mental state, physical state, emotional condition, physical status 904; and (3) overlaying a therapeutic label to the digital content corresponding to the selected condition 906.

The uploaded content (digital content) may be at least one of an application-selected content and user-selected content. Additionally, the uploaded content may be at least one of a created content and curated content. Created content is any type of material in print or digital form that is at least one of selected, sorted, parsed, edited, and processed by at least one of the application and uploaded user. On the other hand, curated content is any type of material in print or digital form that is at least one of built, engineered, designed, and created by at least one of the application and uploaded user. Furthermore, the uploaded content may further contain an animation, infographic, meme, GIF, chat, post, augmented reality/virtual reality expressions, and audio. The digital content uploaded by the user is originated from at least one of a stored, received, visited, curated, and created source.

The selected condition may be an EMS (emotional mental state indicator) indicating at least one of a feeling, sensation, type of discomfort, mood, mental state, emotional condition, or physical status of the user 508. Once the EMS is defined and labeled, the method may then call for pushing at least a subsequent or battery of messages/content personalized to the user based on the initially labeled EMS 509. In some embodiments, the system or method may call for pushing at least a subsequent message or battery of messages personalized to the user based on a user response or interaction to the uploaded digital content and, or to the pushed primary/initial/level message. User response or interaction may be based on a threshold-grade match of the user response to the uploaded digital content and, or to the pushed primary-level message with at least one stored response coupled to a stored uploaded content/primary-level message, whereby the user and stored response is a measure of at least one of a reaction, compliance, engagement, or interactivity with the uploaded digital content and, or pushed primary-level message. Much like the uploaded digital content—whether simply uploaded, created, or curated—the primary message or primary-level message and the subsequent/battery messages may also contain at least one of a text, image, sound, video, art asset, suggested action or recommended behavior. The digital content may further contain an animation, infographic, meme, GIF, chat, post, and audio. The digital content uploaded by the user is originated from at least one of a stored, received, visited, curated, and created source.

In continuing reference to FIG. 16, the prescribed label overlaid on the uploaded digital content may be at least one of a drug type, neurotransmitter type, therapeutic type matched to the selected EMS type. In other embodiments, the EMS may encompass not only the condition, but also the drug type, neurotransmitter type, and, or therapeutic type (cure). In other embodiments, at least one of the EMS type, condition, cure may be based on a scored or color-coded aspects to indicate severity. Assessing an indication score or color-coded range to further convey at least one of an EMS severity, intended effect range, and therapeutic efficacy may be possible. In some embodiments, the efficaciousness or therapeutic value of the uploaded content, primary, and, or secondary messages are validated by at least one—and typically two—independent sources of clinical research or peer-reviewed science, as verified by a credentialed EMS expert.

Figure 17:
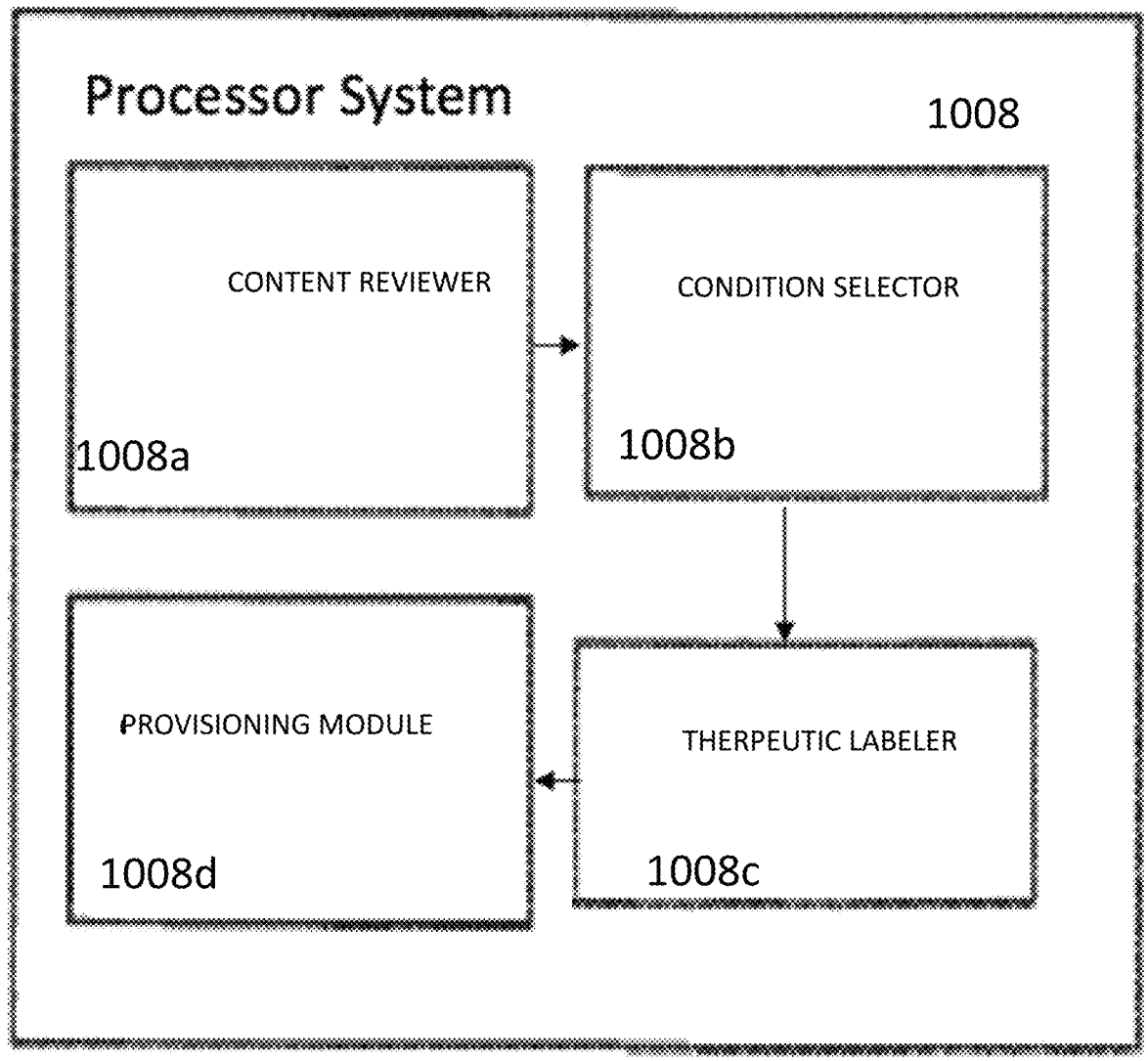
FIG. 17 illustrates a representative block diagram of the therapeutic labeler system in accordance with an aspect of the invention.

Now in reference to FIG. 17, a system depicted as a block diagram, wherein the processing system (1008) and modules (1008a-d) are specifically interrelated and configured to perform a particular sub-routine in accordance with at least one of a defined logic, probabilistic learning (machine learning/AI), statistical modeling, or rules, in order to achieve labeling of a therapeutic value to an uploaded digital content. In one embodiment, the user may upload the content and select the content type and treatment type (FIG. 19). Examples of content type may be video, music, film clip, GIF, photo, PDF, screen shot, social media post, text message template, VR asset, AR asset. The user may choose on or more of the content types to inform more accurate therapeutic labeling of the uploaded content. Upon choosing the content type, the user may choose one or more treatment or condition types (EMS) that most correlate with the uploaded content. In some embodiments, a user may only need to choose the treatment/condition (EMS) type.

In continuing reference to FIG. 17, the content type and treatment type may be autonomously generated without user input or data. The content reviewer 1008a may take multiple bound-boxed crops from at least one of a 2D or 3D parsed or non-parsed image frame, perform object or event detection, and then join crops to form a mask for the original image. The reconstructed mask or loose crops are then stitched together and based on at least one of an object detected, facial feature, overall context, emotional cues, stylistic elements, deconstructed text and, or audio, at least one condition/EMS from a plurality of conditions/EMS is selected by the condition selector 1008b, said selected condition indicating at least one of a feeling, sensation, mood, mental state, physical state, emotional condition, physical status. Once the appropriate condition/EMS is selected, the therapeutic labeler 1008c will assign a therapeutic label to the digital content corresponding to the selected condition by the therapeutic labeler based on a severity-graded look-up table (represented on a high-level and without severity-grading by the quick reference guide—FIG. 23.

While not shown in FIG. 17, the method or system may comprise an option to upload a digital content by a user; parse the uploaded digital content into frames for object/event identification. In some embodiments, object/event identification comprises isolating individual frame into cropped defined structures by the content reviewer. In some embodiments, processing the cropped frames through at least one of a convolutional classifier network or convolutional semantic segmentation network. In other embodiments, object/event identification does not require processing using a convolutional classifier network or convolutional segmentation network. Once identified (i) or identified/processed (i-p), match at least one (i/i-p) frame against a library of stored content indicating at least one selected condition by the condition selector, said condition being at least one of a feeling, sensation, mood, mental state, physical state, emotional condition, physical status. Finally, overlay a therapeutic label to the uploaded digital content corresponding to the stored content with selected condition above a matched threshold by the therapeutic labeler.

At least one of content review, condition selection, and therapeutic labeling may be achieved by analyzing at least one of computed pixel values derived from at least one of a parameter from a threshold-grade event or object by referencing against at least one of a pre-defined, user-defined, and, or learned reference table of recognized object/event-computed pixel values. Any number of may employ machine learning to update any one of a threshold of computed pixel values for object/event detection and, or update any one of a reference analysis of computed pixel values for condition selection/therapeutic labeling. Examples of machine learning may be at least one of a convolution neural network, associated model, training data set, feed-forward neural network, and, or back-propagated neural network.

Still in reference to FIG. 17, the system may further comprise a pushed name or list of names of in-network or out-of-network members with at least one of a self-identified or system-generated EMS receptive to the labeled content, with an option to send the labeled content to at least one of the pushed name or list of names. In other embodiments, a blind push of the labeled content to at least one of the pushed name or list of names may be possible. Furthermore, the in-network or out-of-network member receiving the labeled content may be tracked by at least one of an off-board camera, sensor, compliance or performance to at least one of a cognitive or physical task request.

In other embodiments, the primary prescriber 305 may be used to do at least one of a content review, condition/EMS selection, and overlay of a therapeutic label to a digital content. Assigning a second message to the same user in the same session for the first defined EMS type. The primary prescriber 305 may perform at least one of a content review, condition/EMS selection, and therapeutic label overlay in a logic-defined or rule-based manner, wherein gathered, contextualized, or profiled data may further inform at least one of the content review, condition/EMS selection, and overlay.

Figure 20:
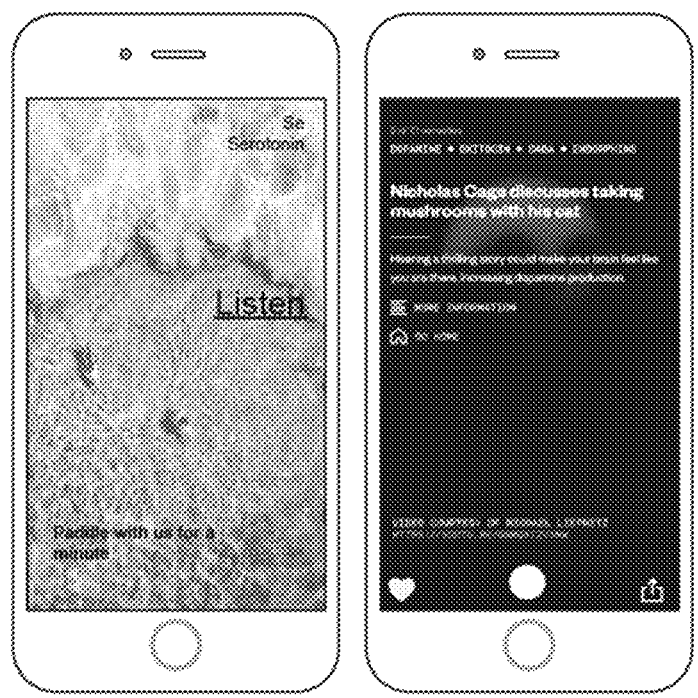
FIG. 20 illustrates a representative screen shot of a downstream sequence of the therapeutic labeler in accordance with an aspect of the invention.
Figure 21:
FIG. 21 illustrates a representative screen shot of a downstream sequence of the therapeutic labeler in accordance with an aspect of the invention.

For instance, when a system-generated EMS is selected as 'Love' for user A, a primary prescriber 305 or therapeutic labeler 1008c assigns a therapeutic label (Serotonin: uplifting and inspiring message to stabilize mood and provide stability for happiness to flourish). In a preferred embodiment, the therapeutic label may also be tapped for providing additional information, such as drug/neurotransmitter information, benefits, and citations (FIG. 20). In one embodiment, a secondary prescriber 307 may push a subsequent message or content, such as a pro-social behavior, such as a local community service, immediately upon a touch interaction with the first inspiring message pushed. In other embodiments, a level of engagement, interaction or compliance may be tracked by the system to infer severity of the EMS. For instance, if user A does not comply with the touch-interaction requests from the first inspiring message or pro-social behavior recommendation of the second message, then the secondary prescriber 307 may push a less physically strenuous pro-social recommendation, such as suggesting to call an in-network licensed expert or simply make a cash donation to a charitable organization of the users choosing via a linked micro-payment method. For the purposes of inferring severity of EMS, any number of diagnostics that leverage any one of the on-device tools may be used, such as gyroscopic sensors or cameras. Severity may also be inferred from contextual data gathered from off-board devices, Iot objects, crawled social media data, etc.

In one embodiment, therapeutic labeling of uploaded digital content may be based on learned user history, such as previous labeling history and, or engagement/reaction (compliance/non-compliance) to receiving a message/content. Based on such history of labeling and, or engagement, a prescriber 307 or therapeutic labeler 1008c may assign a therapeutic label for uploaded content by user A that is consistent or departed from the previous labeling.

Figure 18:
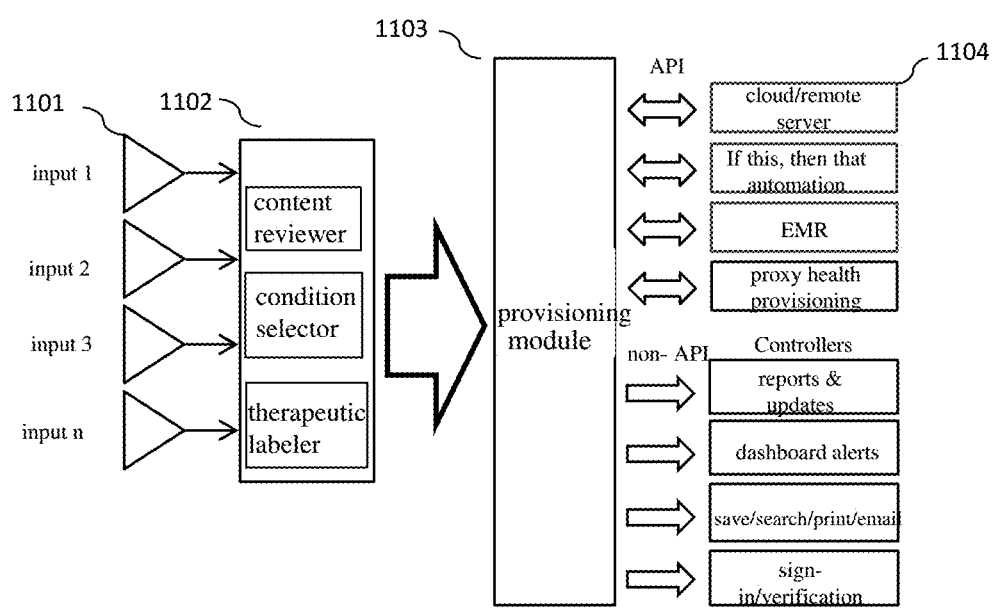
FIG. 18 illustrates a representative interaction flow of the therapeutic labeler system in accordance with an aspect of the invention.

FIG. 18 is a representative interaction flow of the therapeutic labeler system in accordance with an aspect of the invention. In a preferred embodiment of the invention, the inputs 1101 recognizes a command and processes input from anyone of a user's device or user, wherein the input is any one of a digital content uploaded from a user. The digital content uploaded by the user is originated from at least one of a stored, received, visited, curated, and created source. Furthermore, the content may be at least one of saved, processed, edited, and uploaded in edited form; or uploaded in original/received form; and forwarded to the downstream system that provides the recognized command for enabling therapeutic labeling of the digital content.

In an embodiment of the invention, the inputs 1101 may be motion characteristics corresponding to at least one of, physical activity, physiological and sleep related characteristics of a user quantified from a body worn or user device. Additionally, inputs 1101 may account for environmental conditions, such as wind velocity, temperature, humidity, aridness, light, darkness, noise pollution, exposure to UV, airborne pollution and radioactivity quantified from a body-worn/user device and, or remote stations. Further yet, data generated from a periodic survey pushed to a body worn/user device may be used to generate a behavioral profile of the user, which may serve as an input 1101 or inform an input 1101. The system may flag a threshold discrepancy between a composite behavioral profile and a reference behavioral profile to detect or select an appropriate condition/EMS, in addition to the parsed digital content by the content reviewer 1102, condition selector 1102, therapeutic labeler 1102, whereby the appropriate condition/EMS is determined by machine learning algorithms to trigger a number of downstream provisionings 1104.

Further yet, in another embodiment, the system may further comprise integration with any one of a third-party application via an Application Program Interface (API) 1104. This allows for 3rd party database integration, such as Electronic Medical Records (EMR), health monitoring, proxy health provisioning, remote server and, or a cloud based server for other downstream analytics and provisioning. Additionally, the completed automated responses may be saved onto a remote cloud based server for easy access for data acquisition and archival analytics for future use.

In another embodiment of the invention, the system may allow for easy saving, searching, printing, and sharing of completed automated response information with authorized participants. Additionally, the system may allow for non-API applications, for example, building reports and updates, create dashboard alerts as well as sign in/verifications 1104. Alternatively, sharing may be possible with less discrimination based on select privacy filters. Moreover, the system may be integrated with certain workflow automation tools, prompting the system to perform a task command, provided a trigger is activated based on the threshold discrepancy. In an embodiment of the invention, at least one conditional event triggers at least one action controlled by a "if this, then that" 1104 script manager. Further yet, the "if this, then that" 1104 script manager is embedded with an "and, or" trigger or action operators, allowing increased triggers or actions in a command set.

Figure 22:
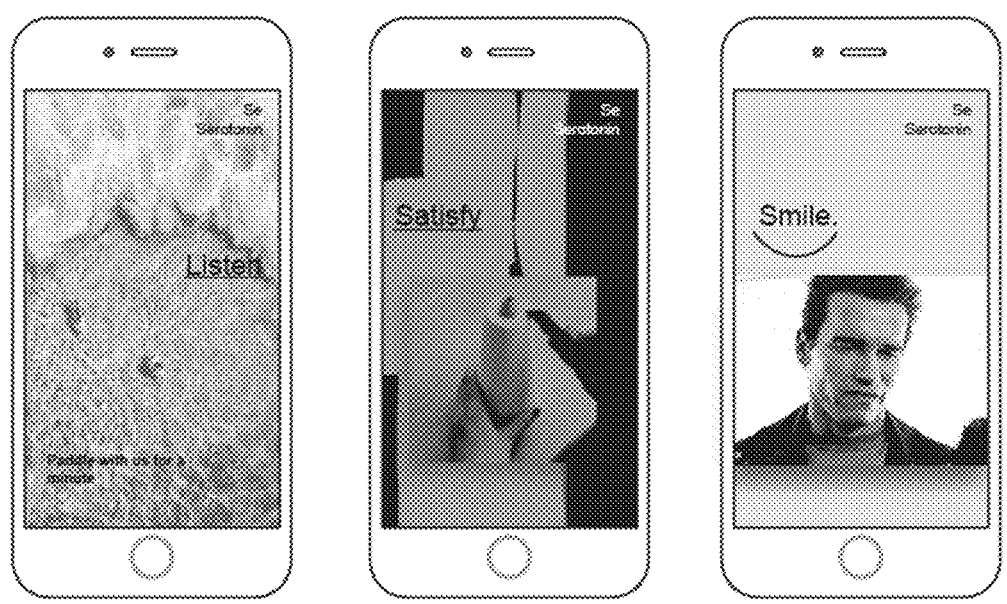
FIG. 22 illustrates a representative screen shot of a downstream sequence of the therapeutic labeler in accordance with an aspect of the invention.

In another instance, the script manager may be embedded with a "if, this, then that" as well as a "and, or" trigger or action operator for increased triggers either downstream or upstream of a command set. While not shown in FIG. 18, "IF" a user uploads content with an EMS rating of sad, "THEN", the user will be sent prescriptive content to counter the sadness, such as Serotonin boosting content (see FIG. 22 as a representative screenshot) "AND" the users closest friend will receive an email/text reminder to get in touch with the user. All of the commands are automatically triggered once an "IF" conditional event is reached.

In yet another embodiment of the invention, "OR" operators may be used instead of the "AND" operator. Further, any number of "AND" and, or "OR" operator may be used in a command function. Such an automation layer may add further efficiencies. An ecosystem of apps may provide for a API-mediated link to the system for enhanced co-interactivity among users network, diagnostics, and other measurables.

The processer system 1102 may further be communicatively coupled to at least one of a provisioning module 1103, interface module, display module, input module, logic module, a context module, timeline module, tracking module, notification module, payment/gifting module, and marketplace module in order to effectuate any number of remote provisioning. In accordance with one aspect, the notification module may be configured to generate reports at regular intervals (such as daily at 12:00 PM, weekly and monthly), on-demand (when the user requests for a report corresponding to the user), when triggered by an event, or upon a detected severe EMS. In an embodiment of the present invention, the notification module may also be configured to send a notification to the user or to a chosen loved one of the user. The notification may be a message, a phone call or any other communication means.

In an embodiment of the present invention, a timeline module may push already pushed messages in at least one of a static, dynamic, and, or scheduled fashion based on at least one of the user's scheduler criteria. The line of static, dynamic, and, or scheduled messages may be curated by the user, pre-set, or dynamically pushed based on any one of a user parameter. In some embodiments, the timeline module enables the displayed line of static, dynamic, and, or scheduled messages to be further replicated on at least one of a social media timelines or stories. In other words, the timeline module enables the displayed messages to be further shared with social media outlets.

In an embodiment of the present invention, a payment or gifting module may enable purchasing and gifting donations, physical objects, or digital assets. In an embodiment of the present invention, a marketplace module may enable purchasing digital assets. The gifting and marketplace module may further be coupled to a distributive digital ledger, wherein each transaction among any user is represented as a unique node in the digital ledger. Each node tagged with meta data facilitating at least one of a transaction, validation and, or registration for each transaction.

Figure 24:
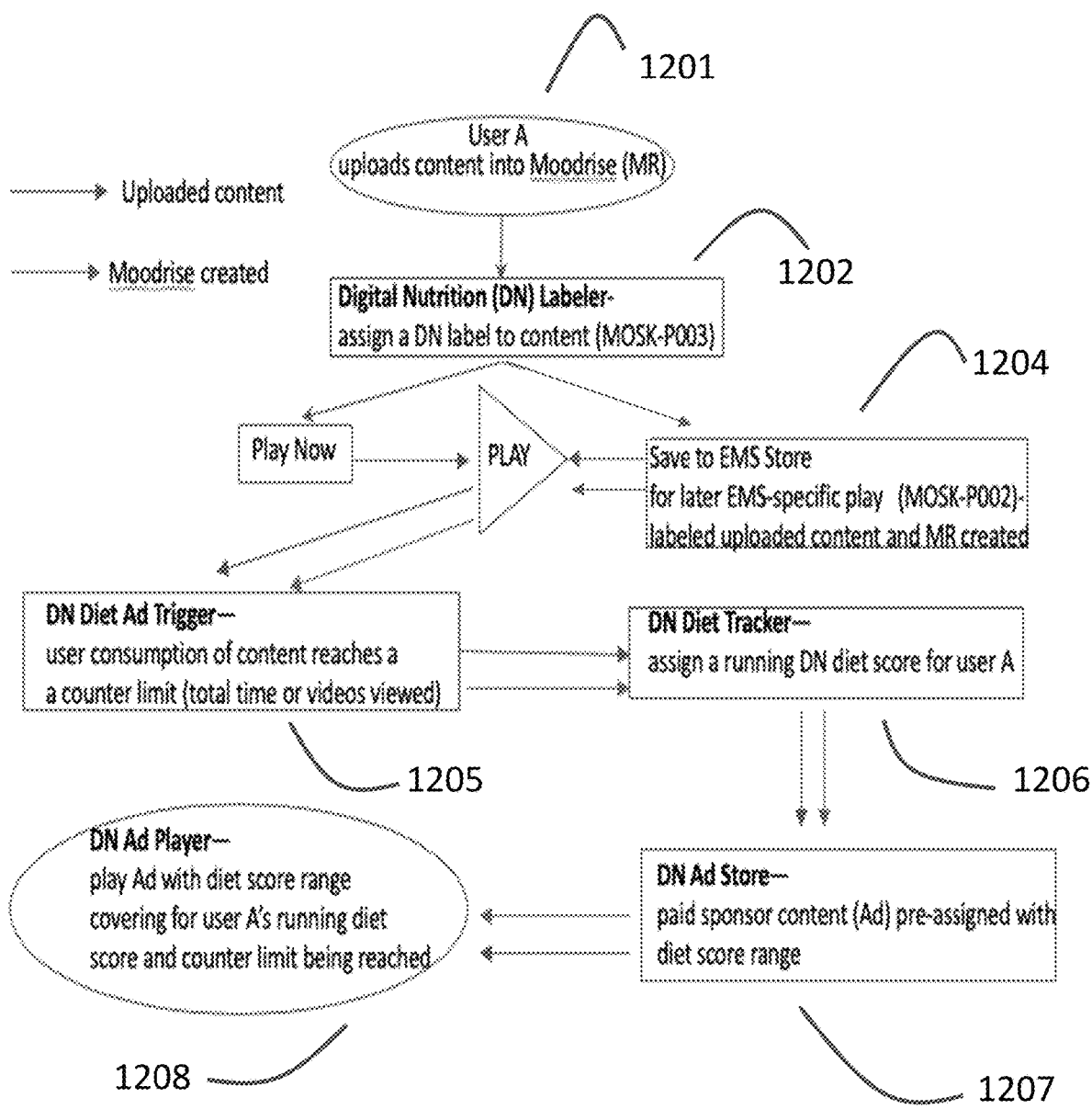
FIG. 24 illustrates a representative process flow diagram of the Digital Nutrition (DN) diet score tracking for targeted ad delivery in accordance with an aspect of the invention.

FIG. 24 illustrates a representative process flow diagram of the Digital Nutrition (DN) diet score tracking for targeted ad delivery in accordance with an aspect of the invention. Digital Nutrition is any deliberate, positive, and productive channel, service, training regimen, or content type, designed to address or alleviate undesirable feelings or mood states.

Figure 25:
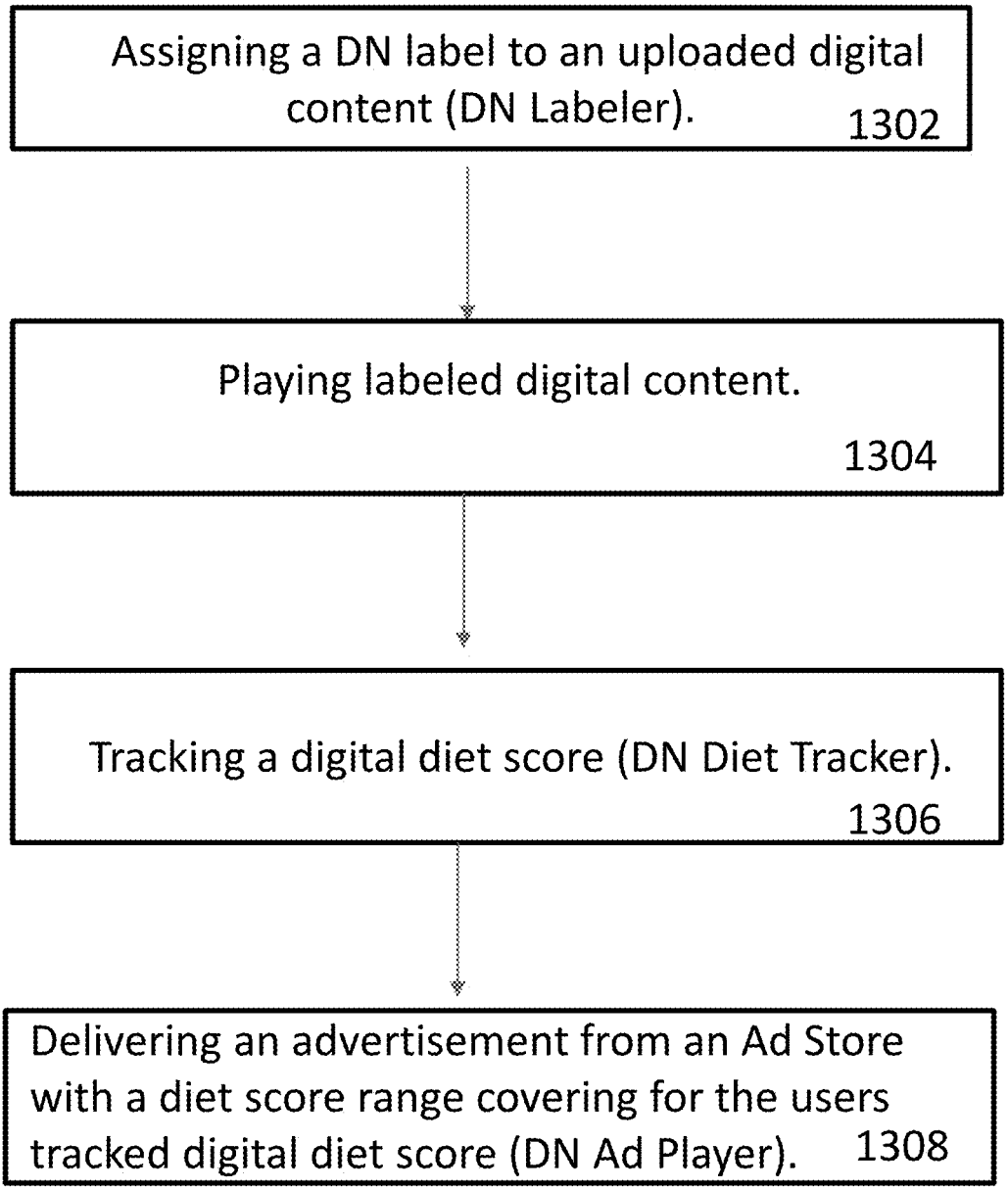
FIG. 25 illustrates a representative method flow diagram of the Digital Nutrition (DN) diet score tracking for targeted ad delivery in accordance with an aspect of the invention.
Figure 26:
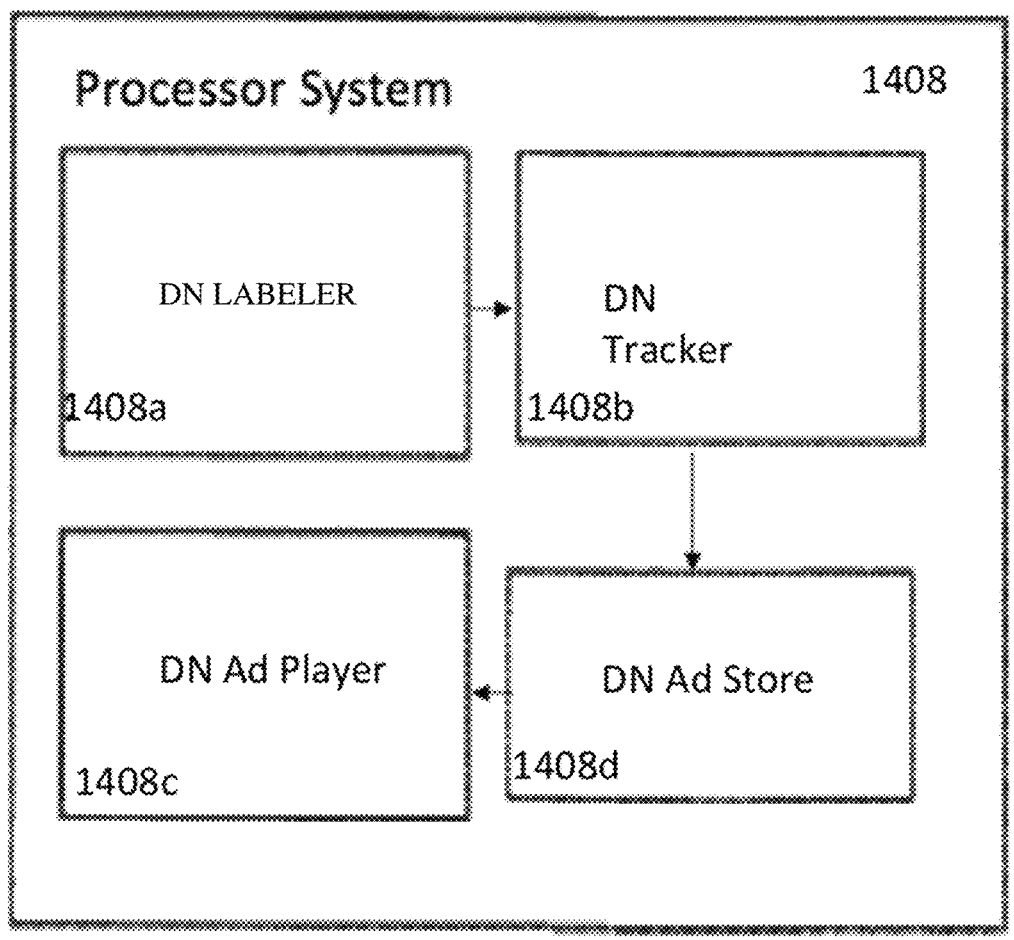
FIG. 26 illustrates a representative system diagram of the Digital Nutrition (DN) diet score tracker for targeted ad delivery in accordance with an aspect of the invention.

Digital Nutrition is proactive, and constitutes the underpinning of any approach to comprehensive wellness. FIG. 25 illustrates a representative method flow diagram of the DN diet score tracking for targeted ad delivery in accordance with an aspect of the invention. Finally, FIG. 26 illustrates a representative system diagram of the DN diet score tracker for targeted ad delivery also in accordance with an aspect of the invention. On a high level, all three figures detail the flow of DN tracking/delivery steps and interaction flow between DN tracking/delivery modules for delivering a targeted advertisement based on tracked psycho-emotional effects of digital content. The first step involves: uploading a digital content by a user 1201; secondly, assigning a digital nutrition (DN) label to the uploaded digital content 1202, 1302 by the DN labeler 1408*a*, wherein said label is an indication of the intended psycho-emotional effect of said content; thirdly, tracking a digital diet score for the user 1206, 1306 by the DN diet score tracker (DN tracker or tracker) 1408*b*, wherein said score reflects at least one of an aggregation, moving average, or most recently viewed labeled content prior to an advertisement trigger 1205; and lastly, triggering delivery of a targeted advertisement 1208, 1308, 1408*d* from a store 1207, 1408*c*, wherein the targeted advertisement is labeled with a digital diet score range covering for the tracked digital diet score of the user.

Alternatively, the first step in the flow may be: uploading a digital content by a user; secondly, assigning a digital nutrition (DN) label to the uploaded digital content, wherein said label is an indication of the intended psycho-emotional effect of said content; and lastly, triggering delivery of a targeted advertisement from a store, wherein the targeted advertisement is triggered based on a counter threshold being reached and is matched to the last viewed labeled content based on a match of label types or group.

The uploaded content (digital content) may be at least one of an application-selected content and user-selected content. Additionally, the uploaded content may be at least one of a created content and curated content. Created content is any type of material in print or digital form that is at least one of selected, sorted, parsed, edited, and processed by at least one of the application and uploaded user. On the other hand, curated content is any type of material in print or digital form that is at least one of built, engineered, designed, and created by at least one of the application and uploaded user. Furthermore, the uploaded content may further contain an animation, infographic, meme, GIF, chat, post, augmented reality/virtual reality expressions, image, video, text, and audio. The digital content uploaded by the user is originated from at least one of a stored, received, visited, curated, and created source.

The method or system may comprise an option to upload a digital content by a user; parse the uploaded digital content into frames for object/event identification. In some embodiments, object/event identification comprises isolating individual frame into cropped defined structures by the content reviewer. In some embodiments, processing the cropped frames through at least one of a convolutional classifier network or convolutional semantic segmentation network. In other embodiments, object/event identification does not require processing using a convolutional classifier network or convolutional segmentation network. Once identified (i) or identified/processed (i-p), match at least one (i/i-p) frame against a library of stored content indicating at least one selected emotional/mental state (EMS cue) or intended psycho-emotional effect by the condition selector, said condition/effect being at least one of a feeling, sensation, mood, mental state, physical state, emotional condition, physical status. Finally, overlay a therapeutic label or Digital Nutrition (DN) label to the uploaded digital content corresponding to the stored content with selected condition/effect above a matched threshold by the therapeutic or DN labeler 1408*a*.

At least one of content review, condition selection, and DN labeling may be achieved by analyzing at least one of computed pixel values derived from at least one of a parameter from a threshold-grade event or object by referencing against at least one of a pre-defined, user-defined, and, or learned reference table of recognized object/event-computed pixel values. Any number of machine learning techniques may be employed to update any one of a threshold of computed pixel values for object/event detection and, or update any one of a reference analysis of computed pixel values for condition selection/therapeutic labeling. Examples of machine learning may be at least one of a convolution neural network, associated model, training data set, feed-forward neural network, and, or back-propagated neural network. Alternatively, content review, condition/EMS selection, and DN labeling may be performed in a logic-defined or rule-based manner. Furthermore, gathered, contextualized, or profiled data may further inform at least one of the content review, condition/EMS selection, and DN label overlay.

Figure 27:
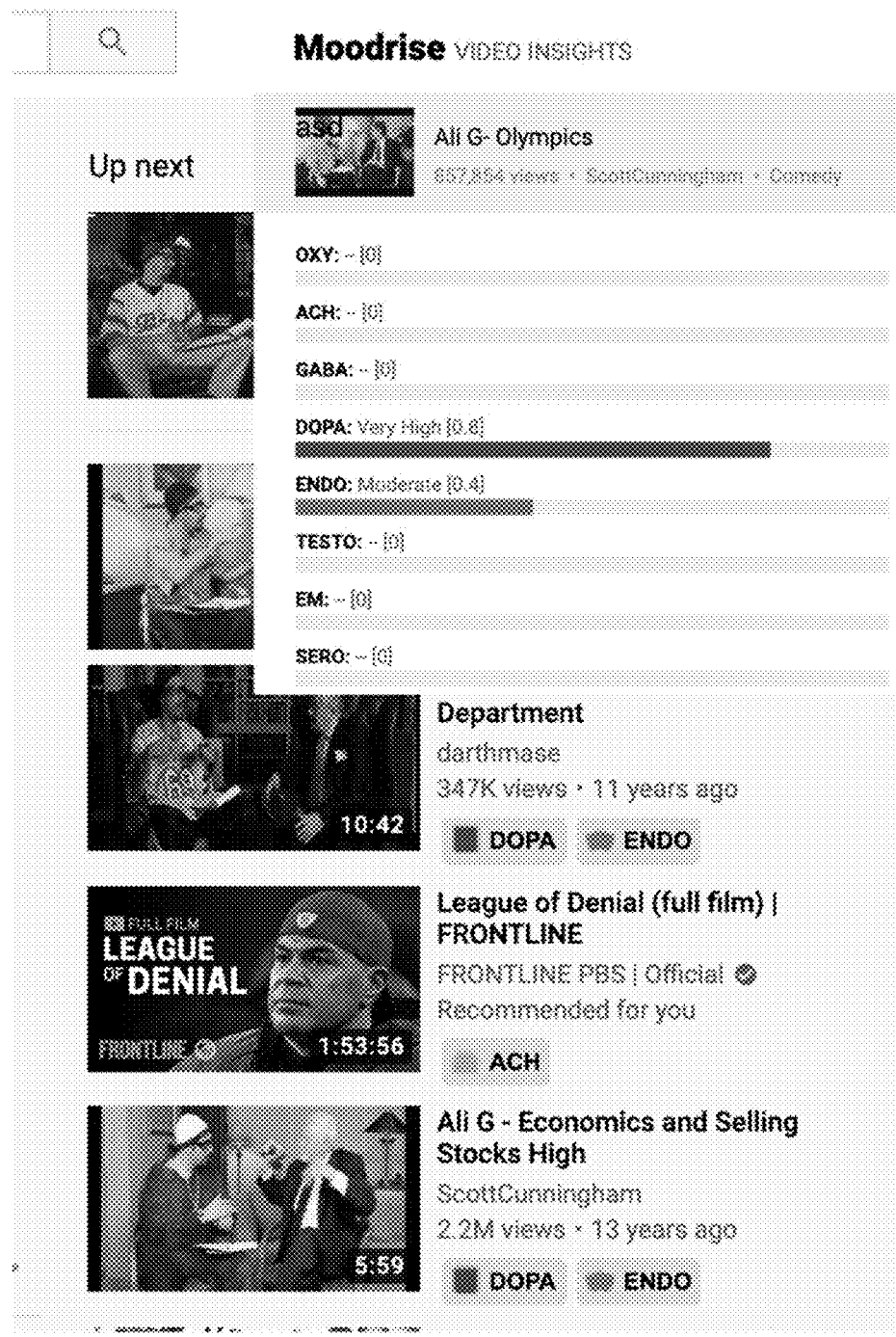
FIG. 27 illustrates a representative system diagram of the Digital Nutrition (DN) diet score for targeted ad delivery in accordance with an aspect of the invention.

For example, Zeeshan may be come across a video on-line and prior to viewing it, upload it into the Moodrise DN loader or labeler for DN labeling. After review/parsing, the labeler may label the content—rich with D.I.Y home improvement tips—with a score of 63, which corresponds to a contemplative, focus-centric psycho-emotional effect potential. In other embodiments, Zeshan's D.I.Y. video may be labeled textually with "contemplative, focus-centric psycho-emotional effect potentially elicited". This psycho-emotional effect may be labelled as seen in FIG. 27, where one can see that Dopamine is very high with a moderate level of ENDO. In yet other embodiments, the D.I.Y. content may be labeled with the neurotransmitter most often associated with enhancing or curing focus or focus-related issues—Acetylcholine or Ach, for instance. In yet other embodiments, the score or label may further be refined to reflect a severity or grade of general psycho-emotional effect (EMS/PEE). For instance, suppose Zeeshan's D.I.Y. video consists of intricate millwork demanding an appreciable amount of craftmanship, the EMS/PEE labeled or assigned may be Ach+++, as opposed to just Ach. Furthermore, once Zeeshan is informed that the millwork D.I.Y. video has been labeled with an Ach+++, Zeeshan opts to save the video to the EMS store—archived by EMS or EMS/PEE—for future playback at a more convenient time.

Labeling by the labeler 1408*a*, may further be informed by the original source or publisher of the content. For instance, since the D.I.Y. millwork video was downloaded for the Moodrise (MR) uploader from the Home Depot website, this meta or conetxual data may further inform the labeler 1408*a* in assessing the 'focus-centric', '63', 'ACh+++' label. In some embodiments, Zeeshan may directly stream the video content from the Home Depot site for the MR labeler 1408*a* to review/parse/label prior to the content being viewable or concomitantly. Once the content is labeled for immediate or future playback, the content may be saved in the EMS store, indexed by EMS/PEE, for future requested playback, MR provisioned, and/or more efficient tracking of viewed content for targeted ad delivery.

The user may be assigned a DN diet score, which is generated by the DN diet score tracker (tracker) 1408*b* based on at least one of an aggregation, moving average, or last viewed labeled content. In one scenario, Yitzhak having just viewed three distinct clips—two of which are generally action/thrilling and one of which is largely dramatic/politically conscious—the tracker may calculate a score of 76 reflecting the overall emotion/mental state cue (overall intended psycho-emotional effect of the content in the aggregate) and deliver an advertisement clip with a diet score range of 72-78, which corresponds to an ad clip featuring a thrill-seeking element (Red Bull ad featuring a freestyling sports-biker, for instance).

In another embodiment, ad retrieval from the DN Ad store 1408*d* for triggered delivery by the DN Ad player 1408*c* is not score or range specific, but rather, just based on broad EMS/PEE grouping. For instance, returning to the scenario of Zeeshan, his ACh+++ labeled content was not off-set by the following short-clip of Luca Doncic crossing over an opponent rated by the labeler several weeks ago with a 'Dopamine' or 'DA'. As a result, the tracker 1408*b* has tracked Zeeshan over the past two views with a psyhoemotional effect evoked (EMS/PEE) of a ACh+. With this slightly revised down 'ACh+' EMS/PEE rating, the DN tracker 1408*b* or DN Player 1408*c* retrieves an Ethan Allen spot for a patio set rated ACh-ACh++. In other embodiments, Zeeshan's tracked ACh+ rating will retrieve a "Cool Grey" Jumpman retro 4 ad based on the fact that one of the two views prominently featured Luka Doncic wearing grey basketball sneakers. This type of object detection and matching similar objects from an ad may obviate the need of score matching.

The DN labeling for targeted ad delivery may not require label tracking of viewed content, but rather just assign a digital nutrition (DN) label to the uploaded digital content, wherein said label is an indication of the intended psycho-emotional effect of said content; and trigger delivery of a targeted advertisement from a store, wherein the targeted advertisement is labeled with a digital diet score range covering for a score corresponding to the last viewed labeled content prior to an advertisement delivery trigger point. Tracking is obviated by simply relying on a 'last content viewed' approach. For instance, in the scenario above, since the millwork clip rated with a ACh+++ was the last seen clip by Zeeshan prior to the DN trigger recognizing a counter threshold (max limit of number of clips/content or duration) being reached, the DN Player 1408*c* will play the Ethan Allen patio spot or any other ad with a comparable ACh-ACh++ rating from the DN Ad Store 1408*d*.

To further clarify, in continuing reference to Yitzhak, though his last viewed content was action/thrill-seeking/DA++ rated (man swimming to train for an upcoming triathalon), a Serotonin/5-HT3 rated ad featuring an elderly man fishing against a soothing backdrop for an Acid-Reflux over-the-counter generic may be pushed by the Ad Player, rather than the Red Bull spot, for its countering effect or value. Though countering the DA++ rating of the viewed content, the Ad Player decision to choose a 5-HT3 rated ad with a common water feature truly reflects the level of nuance that may be incorporated in the delivery of targeted advertising. In addition to labeling, retrieval and delivery of targeted advertising may further take advantage of profile data or contextual data (geo-location, date/time, temperature, sensor-captured data, etc.) to further personalize for maximal branding impact.

In an embodiment, delivery of the ad precedes content viewing. For example, in case of Jen, who is an avid runner, vegan and a pet lover. Jen viewed a documentary on blind people competing on a iron man and was highly inspired to run an ironman releasing a rush of adrenaline. Next morning Jen came across a video—, but prior to viewing she uploaded it on the Moodrise App DN loader or labeler for DN labeling. After review/parsing, the labeler may label the content—bungee jumping of a man into a river gorge, a score of 89 which corresponds to thrill seeking and fun—increase in adrenaline. Based on Jen's last viewed content of the ironman, the DN Ad store would push content for adrenaline the FitBit commercial video before viewing the content of—bungee jumping of a man into a river. Additionally, the match maybe based on labels meaning the Fitbit commercial labels are a match to the labels on the content video.

In an alternative embodiment, the match may not be based on matched content labels. The user has the discretion to choose an ad based on a completely different labelled content. For example, Jen who normally is trilled watching content that would increase adrenalin, may choose to view a soothing content—cascading waterfalls with chirping birds—Calm Inc. ad before she views the adrenaline rich high-octane skydiving content.

Additionally, the content labels may be labelled independent of the EMS/neurotransmitters. For example, in a Sherwin William commercial with a room painted yellow would match a content video—girl in a sunflower field. Both of these would have the color yellow in common thus, similar content label. The color yellow creates an uplifting effect on the mood making one feel happy and optimistic and thus, an increase in dopamine.

In another embodiment, content labelling and delivery of ad decisions may be based on an ad experience which the user may choose to play. For example, Jen wants to experience buying/selling a car from a seller's perspective. She would choose to watch a Carvana—buying and selling cars—ad before she views her content.

In an alternate embodiment, content labelling and the delivery of ads may not be based on the EMS/neurotransmitters. For example, a color wheel may be used to create content labeling—Blue-yellow color wheel may represent a pleasure and reward thus, a release of dopamine. Additionally, consider a scenario of raindrops on leaves with soothing music would depict a blue-green color on the color wheel and would score an 89 on a scoring system depicting calmness thus releasing GABA. Consider a scenario where Jen was listening to soothing music last night before going to bed—blue on the color wheel to destress. Following morning before her morning meditation—blue on the color wheel—an ad of Calm Inc. would be pushed based on the soothing content viewed last night. Alternatively, in an emergency situation in case of a landslide a deep red color on the color wheel and would score a 94 on the scoring system depicting a rush of adrenaline.

Any one of the content labeling, ad labeling, ad scoring, ad retrieval decisions may be backed by peer-reviewed research for scientific support. Additionally, the content labeling may further comprise options for accessing additional information regarding the label, condition, EMS, EMS/PEE, neurotransmitter, treatment, therapeutic, cure, rational, etc. The platform/App may have an extension for advertisers to preview or sneak peek into the most saved content across the Moodrise community and their corresponding rating, thereby allowing for advertisers to tailor their spots to fit within a particular content silo and target demo.

The claimed invention leverages existing clinical research and proven science (already published in peer-reviewed journals) and repackages insights as content modules or behavioral interventions that are simpler, more seductive, and profoundly more fun than traditional analogue therapies or digital treatment regimen. Described more simply, the system and platform curates existing digital content, and creates entirely new content programs, informed by and centered around techniques proven to boost mood, alleviate anxiety, reduce stress, and improve psychological health or mental fitness by directing users to follow procedures proven to increase the production of beneficial molecules and neurotransmitters like Dopamine, Oxytocin, Acetylcholine, Serotonin, and GABA to deliver positive mood and mind-altering effects. This is, in essence, a purely digital, transorbital drug delivery system. No pills. No powders. Purely digital experiences to positively impact mood, mind and personal sense of well-being.

Embodiments are described at least in part herein with reference to flowchart illustrations and/or block diagrams of methods, systems, and computer program products and data structures according to embodiments of the disclosure. It will be understood that each block of the illustrations, and combinations of blocks, can be implemented by computer program instructions. These computer program instructions may be provided to a processor of a general-purpose computer, special purpose computer, or other programmable data processing apparatus to produce a machine such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus, to produce a computer implemented process such that, the instructions which execute on the computer or other programmable apparatus provide steps for implementing the functions/acts specified in the block or blocks. In general, the word "module" as used herein, refers to logic embodied in hardware or firmware, or to a collection of software instructions, written in a programming language, such as, Java, C, etc. One or more software instructions in the unit may be embedded in firmware. The modules described herein may be implemented as either software and/or hardware modules and may be stored in any type of non-transitory computer-readable medium or other non-transitory storage elements. Some non-limiting examples of non-transitory computer-readable media include CDs, DVDs, BLU-RAY, flash memory, mobile device, remote device, and hard disk drives.

I claim:

1. A method for delivering a targeted advertisement based on tracked psycho-emotional effects of digital content, said method comprising the steps of:
    uploading a digital content by a user;
    assigning a digital nutrition (DN) label to the uploaded digital content, wherein said label is an indication of the intended psycho-emotional effect of said content;
    tracking a digital diet score for the user, wherein said score reflects at least one of an aggregation, moving average, or most recently viewed labeled content prior to an advertisement trigger; and
    triggering delivery of a targeted advertisement from a store, wherein the targeted advertisement is labeled with a digital diet score range covering for the tracked digital diet score of the user.

2. The method of claim 1, wherein the digital content comprises at least one of an animation, infographic, meme, GIF, chat, post, AR/VR asset, text, image, video, or audio derived from at least one of downloaded, stored, received, or visited.

3. The method of claim 1, wherein the digital content played by the user is originated from at least one of a stored, received, visited, curated, and created source.

4. The method of claim 1, wherein at least one of the DN label are supported by at least one independent source of peer-reviewed research.

5. The method of claim 1, wherein the DN label is the intended psycho-emotional effect expressed in terms of an intended neurotransmitter (NT) triggered.

6. The method of claim 1, wherein the DN label further comprises a prompted informational for at least one of a digital content type, intended pyscho-emotional effect, intended neurotransmitter triggered, therapeutics, or behavioral recommendations.

7. The method of claim 1, wherein the DN labeling parses the uploaded digital content into frames of cropped defined structures; process said frames through at least one of a convolutional classifier network or convolutional semantic segmentation network; match at least one processed frame against a library of stored content indicating at least one intended psycho-emotional effect on the user; and assign the DN label to the uploaded digital content matched to the stored and indicated content, wherein the DN label is the intended psycho-emotional effect of the digital content on the user.

8. The method of claim 7, wherein the digital content labeled is based in part by a user context fed from at least one of a geo-location, social media engagement, and sensor-tracked motion or activity.

9. The method of claim 1, wherein the tracking of user consumption of labeled content is based on at least one of an aggregation of a pre-defined time, a moving average of a pre-defined time, or the last viewed labeled content at the advertisement delivery trigger point.

10. The method of claim 9, wherein the tracking is expressed as a score reflective of at least one of the labeled content and/or severity/rated labeled content.

11. The method of claim 9, wherein the advertisement delivery trigger point is based on a counter threshold, wherein the counter threshold is based on a duration of labeled content played or the number of labeled content played.

12. The method of claim 11, wherein the trigger point causes a DN advertisement player to search an DN advertisement store for an advertising content labeled with a DN diet score range covering the users DN diet score for delivery to the user.

13. A method for delivering a targeted advertisement based on tracked psycho-emotional effects of digital content, said method comprising the steps of:
uploading a digital content by a user;
assigning a digital nutrition (DN) label to the uploaded digital content, wherein said label is an indication of the intended psycho-emotional effect of said content; and
triggering delivery of a targeted advertisement from a store, wherein the targeted advertisement is labeled with a digital diet score range covering for a score corresponding to the last viewed labeled content prior to an advertisement delivery trigger point.

14. The method of claim 13, wherein the digital content comprises at least one of an animation, infographic, meme, GIF, chat, post, AR/VR asset, text, image, video, or audio derived from at least one of downloaded, stored, received, or visited.

15. The method of claim 13, wherein the digital content played by the user is originated from at least one of a stored, received, visited, curated, and created source.

16. The method of claim 13, wherein the DN label is the intended psycho-emotional effect expressed in terms of an intended neurotransmitter (NT) triggered.

17. The method of claim 13, wherein the DN label further comprises a prompted informational for at least one of a digital content type, intended pyscho-emotional effect, intended neurotransmitter triggered, therapeutics, or behavioral recommendations.

18. The method of claim 13, wherein the DN labeling parses the uploaded digital content into frames of cropped defined structures; process said frames through at least one of a convolutional classifier network or convolutional semantic segmentation network; match at least one processed frame against a library of stored content indicating at least one intended psycho-emotional effect on the user; and assign the DN label to the uploaded digital content matched to the stored and indicated content, wherein the DN label is the intended psycho-emotional effect of the digital content on the user.

19. The method of claim 13, wherein the digital content labeled is based in part by a user context fed from at least one of a geo-location, social media engagement, and sensor-tracked motion or activity.

20. The method of claim 13, wherein the advertisement delivery trigger point is based on a counter threshold, wherein the counter threshold is based on a duration of labeled content played or the number of labeled content played.

21. The method of claim 20, wherein the advertisement delivery trigger point causes a DN advertisement player to search an DN advertisement store for an advertising content labeled with a DN diet score range covering the users DN diet score for delivery to the user.

22. A system for delivering a targeted advertisement based on tracked psycho-emotional effects of digital content, said system comprising:
a Digital Nutrition (DN) labeler;
a Digital Nutrition (DN) tracker;
a non-transitory storage element coupled to the processor;
encoded instructions stored in the non-transitory storage element, wherein the encoded instructions when implemented by the processor, configure the system to:
uploading a digital content by a user;
assigning a DN label to the uploaded digital content by the DN labeler, wherein said label is an indication of the intended psycho-emotional effect of said content;
tracking a digital diet score for the user, wherein said score reflects at least one of an aggregation, moving average, or most recently viewed labeled content prior to an advertisement trigger by the DN tracker; and
triggering delivery of a targeted advertisement from a store, wherein the targeted advertisement is labeled with a digital diet score range covering for the tracked digital diet score of the user.

23. The system of claim 22, wherein the digital content comprises at least one of an animation, infographic, meme, GIF, chat, post, AR/VR asset, text, image, video, or audio derived from at least one of downloaded, stored, received, or visited.

24. The system of claim 22, wherein the digital content played by the user is originated from at least one of a stored, received, visited, curated, and created source.

25. The system of claim 22, wherein at least one of the DN label are supported by at least one independent source of peer-reviewed research.

26. The system of claim 22, wherein the DN label is the intended psycho-emotional effect expressed in terms of an intended neurotransmitter (NT) triggered.

27. The system of claim 22, wherein the DN label further comprises a prompted informational for at least one of a digital content type, intended pyscho-emotional effect, intended neurotransmitter triggered, therapeutics, or behavioral recommendations.

28. The system of claim 22, wherein the DN labeling parses the uploaded digital content into frames of cropped defined structures; process said frames through at least one of a convolutional classifier network or convolutional semantic segmentation network; match at least one processed frame against a library of stored content indicating at least one intended psycho-emotional effect on the user; and assign the DN label to the uploaded digital content matched to the stored and indicated content, wherein the DN label is the intended psycho-emotional effect of the digital content on the user.

29. The system of claim 28, wherein the digital content labeled is based in part by a user context fed from at least one of a geo-location, social media engagement, and sensor-tracked motion or activity.

30. The method of claim 22, wherein the tracking of user consumption of labeled content is based on at least one of an aggregation of a pre-defined time, a moving average of a pre-defined time, or the last viewed labeled content at the advertisement delivery trigger point.

31. The system of claim 30, wherein the tracking is expressed as a score reflective of at least one of the labeled content and/or severity/rated labeled content.

32. The system of claim 30, wherein the advertisement delivery trigger point is determined by a DN Advertisement Trigger.

33. The system of claim 32, wherein the advertisement delivery trigger point is based on a counter threshold, wherein the counter threshold is based on a duration of labeled content played or the number of labeled content played.

34. The system of claim 33, further comprising a DN advertisement store storing advertising content curated by DN diet score range.

35. The system of claim 34, further comprising a DN advertising player for searching an DN advertisement store for an advertising content labeled with a DN diet score range covering the users DN diet score for delivery to the user upon a trigger point or counter threshold reached.

\* \* \* \* \*